United States Patent
Antich et al.

(10) Patent No.: US 7,611,465 B2
(45) Date of Patent: Nov. 3, 2009

(54) RAPID AND ACCURATE DETECTION OF BONE QUALITY USING ULTRASOUND CRITICAL ANGLE REFLECTOMETRY

(75) Inventors: Peter P. Antich, Richardson, TX (US); Charles Y. C. Pak, Dallas, TX (US); Billy Smith, Dallas, TX (US); Edmond Richer, Dallas, TX (US); Matthew A. Lewis, Farmers Branch, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 839 days.

(21) Appl. No.: 10/630,330

(22) Filed: Jul. 30, 2003

(65) Prior Publication Data

US 2005/0015010 A1  Jan. 20, 2005

Related U.S. Application Data

(60) Provisional application No. 60/487,334, filed on Jul. 15, 2003.

(51) Int. Cl.
*A61B 8/00* (2006.01)
(52) U.S. Cl. .................................. 600/442; 600/437
(58) Field of Classification Search ............. 600/437, 600/442
See application file for complete search history.

(56) References Cited

U.S. PATENT DOCUMENTS

| | | | |
|---|---|---|---|
| 4,701,891 A | 10/1987 | Antich et al. | |
| 4,947,851 A | 8/1990 | Sarvazyan et al. | |
| 5,038,787 A | 8/1991 | Antich et al. | |
| 5,042,492 A | 8/1991 | Dubut | |
| 5,197,475 A | 3/1993 | Antich et al. | |
| 5,228,445 A | 7/1993 | Pak et al. | |
| 5,229,933 A * | 7/1993 | Larson, III | 600/459 |
| 5,230,621 A | 7/1993 | Jacoby | |
| 5,284,143 A | 2/1994 | Rattner | |
| 5,526,815 A | 6/1996 | Granz et al. | |
| 5,762,066 A * | 6/1998 | Law et al. | 600/439 |

(Continued)

FOREIGN PATENT DOCUMENTS

WO   WO 0103773 A1   1/2001

(Continued)

OTHER PUBLICATIONS

Antich, et al., Measurement of Mechanical Properties of Bone Material In Vitro by Ultrasound Reflection: Methodology and Comparison with Ultrasound Transmission, Journal of Bone and Mineral Research, 1991. 6:417-426.

(Continued)

*Primary Examiner*—Brian Casler
*Assistant Examiner*—Jonathan G Cwern
(74) *Attorney, Agent, or Firm*—Edwin S. Flores; Chainey P. Singleton; Chalker Flores, LLP

(57) ABSTRACT

The present invention is an apparatus, method and system for determining the coefficient of elasticity of a target by detecting determining simultaneously two or more critical-angle reflections of an ultrasound wave from the target using an ultrasound transducer that includes a transmitter and two or more receivers and calculating the elasticity coefficients of the target.

29 Claims, 6 Drawing Sheets

U.S. PATENT DOCUMENTS

| | | | |
|---|---|---|---|
| 5,772,596 | A | 6/1998 | Forfitt et al. |
| 5,800,363 | A | 9/1998 | Cheng et al. |
| 5,806,520 | A | 9/1998 | Berger et al. |
| 5,810,731 | A | 9/1998 | Sarvazyan et al. |
| 5,873,845 | A | 2/1999 | Cline et al. |
| 5,895,357 | A * | 4/1999 | Ohtomo ............... 600/449 |
| 6,012,779 | A | 1/2000 | Morris |
| 6,036,646 | A * | 3/2000 | Barthe et al. ........... 600/459 |
| 6,068,538 | A | 5/2000 | Alleyne |
| 6,102,860 | A | 8/2000 | Mooney |
| 6,221,019 | B1 | 4/2001 | Kantorovich |
| 6,322,507 | B1 | 11/2001 | Passi et al. |
| 6,328,695 | B1 | 12/2001 | Vammon et al. |
| 6,352,512 | B1 | 3/2002 | Wilson et al. |
| 6,419,648 | B1 | 7/2002 | Vitek et al. |
| 6,537,220 | B1 | 3/2003 | Friemel et al. |
| 2002/0104370 | A1 | 8/2002 | Steger et al. |
| 2003/0013956 | A1 | 1/2003 | Michaeli |
| 2003/0092987 | A1 | 5/2003 | Hynynen et al. |
| 2005/0004457 | A1 | 1/2005 | Moilanen et al. |
| 2005/0043623 | A1 | 2/2005 | Jurvelin et al. |

FOREIGN PATENT DOCUMENTS

| | | |
|---|---|---|
| WO | WO 02/085214 A1 | 10/2002 |
| WO | WO 03/045251 A1 | 6/2003 |

OTHER PUBLICATIONS

Antich, et al, Measurement of Intrustic Bone Quality In Vivo by Reflection Ultrasound: Correction of Imparied Quality with Slow-Release Sodium Flouride and Calcium Citrate, Journal of Bone and Mineral Research 1993. 8:301-311.

Zerwekh, et al., Assessment By Reflection Ultrasound Method of the Effect in Intermittent Slow-Release Sodium Flouride-Calcium Citrate Therapy on Material Strength of Bone, Journal of Bone and Mineral Research 1991 6:239-244.

Li, et al., Bisphosphonate Treatment Sippresses Not Only Stochastic Remodeling but Also the Targeted Repair of Microdamage, Calif Tissue Int, 2001, 69:281-286.

Liberman, et al., Effect of Oral Alendronate on Bone Mineral Density and the Insidence of Practures in Postmenopausal Osteoporosis, 1995, the New England Journal of Medicine, vol. 333 No. 22.

NIH Consensus, Osteoporosis Prevention, Diagnosis, and Therapy, 2001, vol. 285, No. 6.

Odvina, et al., Severely Suppressed Bone Turnover. A Potential Complication of Alendronate Therapy, 2004, The Journal of Clinical Endocrinology & Metabolism, 90(3):1294-1301.

Susan Ott, Editorial: Long Term Safety of Bisphosphonates, 2005, A journal of Clinical Endocrinology & Metabolism, 90(3):1897-1899.

Pak et al, Treatment of Postmenopausal Osteoporosis with Slow-Release Sodium Fluoride, 1995, Annals of Internal Medicine, vol. 123, No. 6.

Richer, et al., Reduction in Normalized Bone Elasticity Following Long-Term Bisphosphonate Treatment as Measured by Ultrasound Critical Angle Reflectometry, 2005.

EPO Supplementary Search Report for Application No. 04778707.9 dated Jun. 4, 2009.

Antich, P., et al., "Ultrasound critical-angle reflectrometry (UCR): a new modality for functional elastometric imaging," Physics in Medicine and Biology (1997), 42:1763-1777.

Mehta, S. S., et al., "Bone material ultrasound velocity is predictive of whole bone strength," Ultrasound in Medicine and Biology (2001), 27:861-867.

* cited by examiner

PATIENT

NORMAL

RAPID AND ACCURATE DETECTION OF BONE QUALITY USING ULTRASOUND CRITICAL ANGLE REFLECTOMETRY

This application claims priority to pending provisional patent application Ser. No. 60/487,334, filed Jul. 15, 2003. Without limiting the scope of the invention, its background is described with respect to bone quality.

TECHNICAL FIELD OF THE INVENTION

The present invention relates in general to the field of bone quality determination, and more particularly, to the rapid and accurate measurement of elasticity coefficients, in vivo for cortical and trabecular bone.

BACKGROUND OF THE INVENTION

Need for Non-Invasive Measurement of Bone Quality. Osteoporosis is a major medical problem, with a large percentage of elderly persons being susceptible to non-traumatic fractures (bone fractures sustained from minimum trauma). Bone strength is a primary predictor of bone fractures. Bone strength is determined by both bone density and biomechanical aspects bone quality measurable in the laboratory and, in living organism, by ultrasound.

Currently, bone density can be measured by several methods, including: dual energy x-ray absorptiometry and computer-assisted tomography. From epidemiological studies, bone density is inversely correlated with the rate of skeletal fractures. Thus, bone density has been used to define osteoporosis, with a T-score of less than −2.5 (or below about 75% of normal peak value in the lower spine) referred to as osteoporosis even in the absence of fractures.

Recent discoveries, however, have presented situations in which severe impairment of bone quality can occur. Introduced in 1996, a new class of drugs called "bisphosphonate" has been widely used for the treatment of osteoporosis (Liberman et al., *N. Engl. J. Med.* 333:1437-1443, 1995). With long-term use, new studies suggest that these drugs can severely impair bone quality, leading to recurrent fractures that do not heal properly (Ott, *J. Clin. Endo. Metab.* 86:1835, 2001; Odvina, et al., *J. Bone Miner. Res.*, September, 2003; Richer et al., *J. Bone Miner. Res.*, September, 2003; Li et al., *Calc. Tissue Intern.* 69:281-286, 2001). Moreover, with improvement in surgical techniques and in medical treatments to prevent rejection, more patients are living longer after kidney (renal) transplantation. These patients are known to have increased susceptibility to fractures, since they probably have defective bone from taking steroids and suffer from other factors that are harmful to bone. These clinical conditions presented situations wherein a prominent reduction in bone quality may develop.

Another recent development that emphasizes the need for a reliable method to measure bone quality is the recognition that bone quality, aside from bone density, is an important determinant of fractures in osteoporosis. In 1994, the World Health Organization defined osteoporosis based on bone density alone. In 2000, the NIH Consensus Conference on Osteoporosis defined osteoporosis as "a skeletal disorder characterized by compromised bone strength predisposing to an increased risk of fracture".

Needed clearly is a device that can measure reliably, quickly and non-invasively the biomechanical quality of bone in vivo. The device should permit for the rapid, accurate, consistent detection of elasticity and strength data. A need also exists for the development of a system that is automated and which has a design, engineering and software for data acquisition that is user-friendly. Finally, a need has arisen for a reliable, inexpensive method for monitoring the status of a patient's bone quality information during treatment of, e.g., osteoporosis or other conditions.

SUMMARY OF THE INVENTION

The apparatus, method and system of the present invention use ultrasound critical angle reflectometry (UCR) to improve patient care. The present invention uses UCR to calculate bone elasticity coefficients allowing measurement of bone quality more practical and faster than in previous devices. The present invention also expands the method to take explicitly into account the anisotropy of bone, assumed to be hexagonally symmetric. By measuring maximum and minimum elasticity coefficients, the anisotropy can be calculated. The device is designed to make measurements at multiple sites of bone; at each site, cortical and trabecular bone can be separately analyzed for elasticity coefficients and anisotropy. An integral part of the device is a robotic gantry of specific design, constructed to permit the rapid determination of the "normal" (alignment of measuring device perpendicular to bone surface) to bone and to automate the measurement of spectra at different orientations. The normal to bone must be determined with considerable accuracy, as it represents the initial angle (degrees) in the angular system, and thus dominates the accuracy of the measurement. Using this gantry, once the normal has been determined, the head can be rotated using the normal as the axis of rotation to obtain the spectra at different orientations. This activity is now rapid and automated. When made for a specific site, the size of the device can be made smaller, while encompassing the same basic features.

In one embodiment, the present invention is a transducer that includes at least one ultrasound transmitter and two or more receiver elements arranged in an array along a concentric arc that shares a focal point with the transmitter, wherein the receiver array detects simultaneously the reflected ultrasound energy from a target. The transducer may include a transmitter that is concave in at least one dimension and/or two or more receivers that form a concave array in at least one dimension; and/or a transmitter and two or more receivers that are concave and concentric, e.g., about a common focal point. The transducer may have an odd or even number of receiver elements or receivers greater than one, e.g., 2, 4, 8, 16, 24, 36, 48, 64, 128 or more independent receivers. In one embodiment, the two or more receivers form a receiving array system that includes at least one transmitter and a 48-element receiver array located in a housing, wherein the receiver array measures simultaneously the velocity of an ultrasound wave across 120 degrees from a point of examination that is at or about the focal point of the transmitter. The housing for the transmitter and the at least two receivers, have at least one opening at or about the focal point of the transmitter and receivers.

In one embodiment, the transducer includes a housing for the transmitter and the at least two receivers, the housing having at least one opening, a latex membrane at or about the opening of the housing and an ultrasound conductive material within the housing. In one example, the ultrasound conductive material may include water, saline and the like. The transducer may be part of an ultrasound system that further includes a computer-controlled positioning arm connected to the transducer, wherein the movement of the transducer permits accurate positioning of device on a point of examination.

The transducer may also include a pressure detector in communication with the ultrasound conductive material; this system can then detect the rise in pressure within the housing that could break the latex membrane. The computer may be connected to transmitter and receivers of the transducer, the computer including at least one code segment that gathers one or more reflected spectra from each receiver at each angle, and calculates from the spectra the critical angles for a cortical and a trabecular components of bone being examined. From the data acquired, the computer may also include at least one code segment that determines critical angle velocities, and fits them to a linear-quadratic equation for the determination of at least two principal coefficients of elasticity.

Yet another embodiment of the present invention is a transducer that includes at least one ultrasound transmitter and a receiver array that is concentric and shares a focal point with the transmitter, wherein the receiver array detects simultaneously the reflected ultrasound energy from a target at multiple angles. The transducer detects pressure waves that may be used to determine reflected spectra from a bone that is undergoing bone treatment therapy, e.g., for osteoporosis, in order to calculate elasticity coefficients of cortical and a trabecular bone, which can then be used to calculate bone anisotropy of outer hard and inner spongy bone. The critical angle velocities may be used to determine at least two principal coefficients of elasticity, which correlate with bone quality and strength data that may be used to track improvements or degeneration of bone during treatment with, e.g., bisphosphonate, steroid and other therapies.

The present invention also includes a method for determining the coefficient of elasticity of a target, comprising the steps of, detecting simultaneously two or more critical-angle reflections an ultrasound wave from the target using an ultrasound transducer comprising a transmitter and two or more receivers operating over a sufficient angular spectrum for the expected variations in bone properties, and calculating elasticity coefficient of the target. The method for the measurement of critical angle and amplitude herein was described in a prior patent (U.S. Pat. No. 5,038,787). The target may be bone, e.g., from a human being who may be suspected of having osteoporosis. The method may further include the determination of disease progression in a human being known or suspected of having osteoporosis who is treated with osteoporosis-preventing drugs (e.g., bisphosphonate, its salts or mixtures thereof, estrogen, estrogen analogs or selective estrogen receptor modulators, parathyroid hormone peptide, fluoride, vitamin D or calcitonin) or drugs that are known to cause bone loss (e.g., steroid and anticonvulsant). The present invention includes the use of a transducer that is non-invasive. The present invention may be used to determine elasticity coefficients, calculated as the square of the acoustic velocity determined from the critical angle for the intrinsic orientation of bone at a fixed position using values detected at multiple orientations from the ultrasound transducer. Using the maximum elasticity coefficient and a minimum elasticity coefficient, the degree of target anisotropy (e.g., bone anisotropy) may be estimated in a rapid and automated manner. To achieve more reliable results, the apparatus, method and system disclosed herein also include the use of an automated arm to rapidly and consistently determine the normal of the transducer to the target. Data processing and calculations are also made more efficient by the concurrent or simultaneous detection from, e.g., 2, 4, 8, 16, 24, 36, 48, 64 or 128 receivers.

Critical-angle reflection value of an ultrasound wave at two or more receivers that are concentric with a transmitter may also be detected and stored, displayed and/or printed for further analysis. As such, the present method may also include storing the detected critical-angle reflection of ultrasound waves at different points in time and comparing the measurements to track changes in the coefficient of elasticity of the target over time.

The present invention may also be used to determine the effect on a coefficient of elasticity of a bone from a patient undergoing therapy for osteoporosis, comprising the steps of detecting simultaneously two or more critical angles of reflection of ultrasound waves directed at a bone using an ultrasound transducer with one or more transmitters and two or multiple receivers, determining an elasticity coefficient for the bone as the square of the acoustic velocity for the intrinsic orientation of bone at a fixed position using values detected at each of the two or more receivers and calculating the anisotropy of the bone from the elasticity coefficients. The apparatus, method and system disclosed herein may also include the steps of storing a first detected critical-angle reflection of ultrasound waves at two or more receivers prior to, or concurrent with, treatment with a bisphosphonate or derivative thereof, storing a second detected critical-angle reflection of ultrasound waves at two or more receivers after a period of time and comparing the first and second measurements to track changes in the coefficient of elasticity of the bone during treatment with the bisphosphonate or derivative thereof. The detection and calculation of a maximum elasticity coefficient and a minimum elasticity coefficient of a cortical and a trabecular region of the bone may be used to estimate the anisotropy of the bone in vivo, before and during the treatment of a patient with bisphosphonate, and for those patients that do not respond positively to treatment, or that respond negatively to treatment, to identify those patients and change the treatment prior to further damage. The present invention allows the determination of the elasticity of cortical bone, trabecular bone, and anisotropy of a patient's bone in a manner that is non-invasive, e.g., at a patient's heel. Using the data acquired, stored and/or processed, the user may calculate the anisotropy of the bone (determining a maximum elasticity coefficient and a minimum elasticity coefficient of a cortical and a trabecular bone region), wherein the measurements correspond to an axis of a weight-bearing and a non-weight-bearing bone, respectively. Treatment that is tracked by this device may also include other drugs used to treat osteoporosis (e.g., estrogen, estrogen analogs, parathyroid hormone peptide, fluoride, vitamin D and calcitonin) or drugs that can cause bone loss (e.g., steroid and anticonvulsant). This device can also be used to follow diseases or conditions (e.g., Paget's disease and immobilization) that are suspected of having impaired bone quality.

The present invention also includes a system for measuring bone anisotropy that includes a computer-controlled ultrasound critical-angle reflectometry transducer that detects ultrasound velocities at multiple angles simultaneously and automatically, an articulated arm that permits motion in three-dimensions that supports the ultrasound transducer and a computer connected to and capable of receiving a signal from the ultrasound transducer to calculate the critical-angle reflectometry data from the ultrasound transducer. The computer is connected to one or more controllers of the articulated arm that direct the position of the transducer in three dimensions. The transducer may be used to measure the elasticity coefficient of bone from a human being suffering from or suspected of having osteoporosis, e.g, the elasticity coefficients of bone of a human being suffering from or suspected of having osteoporosis treated with bisphosphonate or steroid. The computer can determine an elasticity coefficients from the velocity of an ultrasound wave as determined by UCR, and/or calculate a maximum elasticity coefficient and a minimum elasticity coefficient to estimate a degree of target anisotropy. Using the data, the computer of the present system may also calculate a maximum elasticity coefficient and a minimum elasticity coefficient to estimate a degree of bone anisotropy. To automate the determination of bone anisotropy with results that are rapid and consistent, the computer of the present invention automates the determination of the normal of the transducer to the target. The computer may store a value for a critical-angle reflection of ultrasound waves at different points in time, and even compare and provide the user with a user-friendly output that shows the effect on a coefficient of elasticity of bone from a patient undergoing therapy for osteoporosis by storing a first and a second value for the coefficient of elasticity of a patient at a first and a second point in time, as well as the effect on anisotropy of bone of treatment by storing a first and a second value for anisotropy of a patient at a first and a second point in time.

In yet another embodiment, the system of the present invention determines the effect on a coefficient of elasticity of bone from a patient undergoing bisphosphonate therapy for osteoporosis by storing a first and a second value for the coefficient of elasticity of a patient at a first and a second point in time, and also tracks the effect of treatment on a bone anisotropy value calculated from maximum and minimum elasticity coefficients. Treatment may be other drugs used for osteoporosis as well as those that can cause osteoporosis.

More particularly, the present invention includes a custom designed transducer head, which permits a nearly instantaneous measurement over a complete set of angle of reflection. The head includes two ultrasound elements encased within a water-tight enclosure with an elastic pliant interface (placed over the bone tissue under examination). In one embodiment, the single-element transmitter and the 48-element receiver array are separate. Both are sections of right cylinders of different radii but with a common axis, subtending 120 degrees. The midpoint of the axial segment is the nominal center of the transducers. The two elements are mounted in a fixed geometry within a water-tight solid container, which is filled with water and terminates in a window covered by a latex membrane, in a configuration such that the common center of the transducers projects about 1.5 cm beyond the window. In operation, the liquid is under a slight pressure controlled by gravity (by using a reservoir of water placed at a slight higher elevation than the transducer head on the support base) and the latex membrane bulges at least 0.5 cm beyond the rim of the window. When the bulge is in contact with the patient's skin (overlying bone being examined), the transducer center is a virtual point projected under the skin at depth.

The positioning arm is a pantograph that includes two segments shaped as parallelograms, one attached to the base and one supporting the transducer head. The arm can be moved vertically and horizontally (three degrees of freedom) by means of motors mounted on the base. The arm is articulated so that the transducer head pivots around a fixed point, coincident with the center of the transducers. This geometric property makes it possible to determine the normal by changing the tilt angles $\phi$ and $\theta$ at two mutually orthogonal values of rotation angle $\psi$. In this fashion, the axis of the transducer head can be rotated with two degrees of freedom to coincide with the normal to bone at the fixed point and the transducer head can be rotated by an angle $\psi$ around that axis to assume any orientation along the bone surface.

During an examination, the operator places the transducer head over the site of interest (bone tissue being examined), and the transducer head is advanced by the operator using precise, sub-millimeter steps of the arm using computer controls until the transducer center is at the surface of the bone under study. This advance, for the heel, is restricted to 0.5-1.0 cm, and the patient's skin remains in contact with the flexible membrane and does not come in contact with the rim or any other element of the solid surface. Excessive pressure (which may occur, for example, from a sudden movement of the foot that is being measured) causes the advance to stop and the head to retract. A single (imploding cylindrical) wave is emitted by the transmitter, and each receiving element detects the reflected amplitude over a set of angles of reflection, operationally determined as successive elements of the receiving array. A critical angle $\beta_c$ corresponds to a maximum in this distribution. The velocity V is then given by $V=V_c/\sin\beta_c$ where $V_c$ is the velocity of sound in the calibration medium (water). For each orientation $\psi$, a different value of V is obtained, $V(\psi)$. As bone has an intrinsic hexagonal symmetry, the distribution is determined a priori to be $V(\psi)=A\cos^4\psi+B\cos^2\psi+C$. In classic textbook notations, these are expressed in terms of the elements of the stiffness matrix $\{C\}$ as $A=C_{11}+C_{33}-k$, $B=k-2C_{11}$, $C=C_{11}$ and $k=2(C_{13}+2C_{44})$. The present invention permits the determination of two principal coefficients: $E_{min}=C(=C_{11})$ and $E_{max}=A+B+C(=C_{33})$. These coefficients are intrinsic properties of bone reflective of its mechanical properties.

Thus, key innovations of this UCR transducer and system are: (a) "dual array" system of single transmitter and multiple receiver elements, e.g., 48-receiver elements, which allow simultaneous measurement of critical angle velocities across the whole spectrum of angles of scattering; (b) a robotic arm engineered to accommodate naturally the movements that permit accurate positioning and alignment along the normal to bone of the transducer head over the site of bone tissues being examined; (c) the use of latex membrane containing water in the transducer head avoiding immersion of bone tissue in a water bath, (d) special engineering features that prevent excessive pressure to build on the membrane (enclosing ultrasound-conducive material inside the transducer) or the patient; (e) data acquisition software to obtain the reflected spectra from measurements of the reflected wave train at each angle and to extract from the spectra the critical angles for cortical and trabecular bone; and (f) special post-processing software to determine the critical angle velocity V at each angle $\psi$, and then fit the data onto a linear-quadratic formula relating $V^2$ on the $\cos^2$ of the angle $\psi$, in order to determine two principal coefficients of elasticity.

For example, the apparatus, method and system of the present invention permit for a simple, fast determination of the vector "normal" to the transducer for a more accurate and repeatable measurement. The invention permits the simultaneous and automated detection for the velocity of the sound signal with less dependence on the orientation of the transducer. Furthermore, the system allows for a rapid, automated and fast determination of elasticity coefficients and hence permits, for the first time, a calculation of anisotropy. Using the transducer, methods and system disclosed herein, a more complex and hence more accurate determination and measurement with full automation may be taken at, e.g., 3 points in 6 orientations with a reduction in the time for measurement time of one-third or less than currently possible. The method is non-invasive and does not require immersion of the patient or a patient's body part in an immersion bath containing an ultrasound carrier media. Furthermore, the present invention may be used to determine and track the effect of patient therapy using, e.g., a bisphosphonate, salt or derivatives thereof. Other patients, e.g., patients with renal transplant and those taking other drugs used to treat osteoporosis or drugs that can cause bone loss, will also benefit from the present invention.

The present inventors have recognized that bone density alone is not predictive of the risk of fractures. Some patients with normal bone density develop non-traumatic fractures, and some with low bone density do not sustain fractures. One explanation for this finding is that bone quality may be "out of line" from bone density. Thus, some subjects with low bone density may be less susceptible to fracture, if bone quality is superior. On the other hand, some with high bone density may be susceptible to fractures if bone quality is poor.

Measurement of bone quality is important, because there are some conditions or treatments that are associated with, or may cause, deterioration of bone quality. Examples where bone quality is presumed to be impaired are: Paget's disease of bone (with excessive formation of abnormal bone with fibrosis), osteomalacia or rickets (with poorly mineralized bone), immobilization and fluorosis (toxic fluoride exposure with abnormal mosaic bone). Unfortunately, there is no commercial device that can measure bone quality non-invasively (safely). The available ultrasound method is based on transmission of ultrasound across bone tissue and thus only yields a measure largely of bone density.

Clinical applications of the present invention permit the determination of bone elasticity, anisotropy and strength data. A device capable of measuring elasticity coefficients at different sites of bone has been constructed by the new UCR method, tested in the calcaneus (heel), and its important clinical applications have been identified. With this new UCR device, multiple measurements can be made rapidly and reliably, yielding elasticity coefficients of cortical and trabecular bone non-invasively in vivo (in living persons). The transducer disclosed herein can determine peak and minimum elasticity coefficients, where the maximum elasticity coefficient is an intrinsic property of bone that is critical in weight bearing, and minimum elasticity coefficient is one that is less critical in weight bearing. From the ratio of maximum and minimum elasticity coefficients, anisotropy (asymmetry) of bone can be estimated. This device has shown to be clinically useful in detecting inferior bone quality during treatment with bisphosphonate (a widely used drug for osteoporosis) and in renal transplantation (on steroid treatment). As will be described below, the reductions in bone quality shown in these conditions was much greater than disclosed previously in postmenopausal osteoporosis. The device may also be useful in detecting improvement in bone quality from certain treatments (e.g., low dose intermittent fluoride).

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

Figure 1:
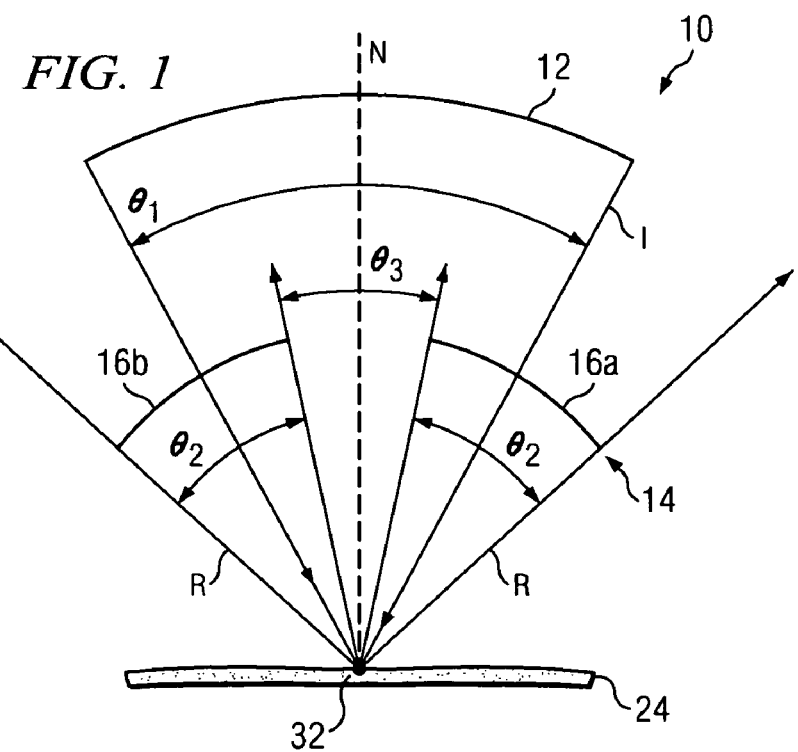
FIGS. 1 and 2 are diagrammatic renderings that show the general principles of UCR using two alternative embodiments of the device and system of the present invention.

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention and do not delimit the scope of the invention.

Ultrasound Critical Angle Reflectometry (UCR). In the early 1990s, the present inventors introduced a novel method, called ultrasound critical-angle reflectometry or UCR, for measuring bone quality based on the "reflection" of ultrasound across small parts of bone surfaces of about 0.2 mm (Antich, et al., *J. Bone Min. Res.* 6:417-426, 1991). Bone quality may be derived or inferred from ultrasound velocity. The original UCR device determined velocity in cortical bone ("hard bone" on outer parts of bone tissue) as well as in trabecular bone ("spongy bone" in the inner core of bone tissue).

The present invention describes an improvement of methods for ultrasound critical-angle reflectometry, which allows a rapid and reliable measurement of elasticity coefficients (quality) of cortical (hard) and trabecular (spongy) bone non-invasively in vivo in human beings. The refinement permits simultaneous detection of reflected ultrasound amplitudes at multiple angles of incidence, and the measurement of ultrasound velocity at critical angle over a range of orientations using a special "array system" and novel engineering and software designs. The software implements from these data the calculation of the principal elasticity coefficients from the square of velocity. Both the maximum elasticity coefficient $C_{33}$ (approximately along the vertical axis, critical in weight-bearing) and minimum elasticity coefficient $C_{11}$ (approximately along the horizontal axis, less critical in weight-bearing) are separately calculated in cortical and trabecular bone. This measurement is more precise than that obtained at a fixed anatomical direction because the intrinsic orientation of bone changes with position, causing the velocity along a given anatomical direction to vary by more than the measurement error, while the velocity along a given intrinsic direction is affected only by measurement uncertainties. As deterministic relationship exists between the square of velocity and the intrinsic orientation, a fit to the values at multiple orientations minimizes the measurement errors. Moreover, the measurement is more accurate because acoustic waves that do not propagate along a principal axis have a mixed nature (they are quasi-pressure waves), obscuring correlations with mechanical properties such as elasticity and strength. From the ratio of maximum and minimum elasticity coefficients, the degree of "anisotropy" (asymmetry) can be accurately estimated. The UCR apparatus and method disclosed herein has been applied to detect impaired bone quality that contributes to osteoporotic fractures.

In patients with kidney transplantations taking steroids, a condition known to be associated with impaired bone quality and increased susceptibility to fractures, cortical and trabecular elasticity coefficients were decreased by 15-30% from the normal premenopausal state. Treatment with bisphosphonate, a widely used drug to treat osteoporosis, can cause "adynamic bone disease" (severe depression of bone turnover) after long-term use, resulting in fractures of long bones that heal poorly. By the new UCR method, the elasticity coefficients of cortical and trabecular bone were also reduced by 15-30% during long-term bisphosphonate treatment, indicative of impaired bone strength. Thus, this invention claims a reliable and rapid method for measuring non-invasively in human beings, the intrinsic (material) quality of cortical and trabecular bone, that is useful in detecting conditions with inferior bone strength, and in alerting to the development of defective bone among patients taking bisphosphonate or steroid.

Three patents have been issued to the present inventors to methods and applications of the original UCR device (U.S. Pat. Nos. 5,038,787, 5,197,475, and 5,228,445, relevant teachings of UCR are incorporated herein by reference). In this approach, ultrasound signal in bone was measured while varying the angle of incidence and analyzing the amplitude of the ultrasound wave reflected by bone. An apparatus that can measure ultrasound velocity at the critical angle was described (Antich, et al., *J. Bone Miner. Res.* 6:417-426, 1991; Antich, et al., *J. Bone Miner. Res.* 8:301-311, 1993). Using this apparatus, ultrasound velocity in trabecular bone was shown to be reduced by 7% in normal postmenopausal women and by 13% in patients with untreated postmenopausal osteoporosis, compared with normal premenopausal women. Treatment with sustained-release sodium fluoride, that increases bone density and inhibit fractures of the spine by delivering therapeutic subtoxic amounts of fluoride (Pak, et al., *Arch. Intern. Med.* 123:401-408, 1995), was found to increase ultrasound velocity of trabecular bone to the level of normal postmenopausal women (Antich, et al., *J. Bone Miner. Res.* 8:301-311, 1993; Zerwekh et al., *J. Bone Miner. Res.* 6:239-244, 1991).

The original UCR device was mounted on a simple gantry that allowed linear motions and rotations; its transducer head may include two transducers moving in unison. While the design was simple, it requires considerable manual adjustments and complex movements in order to measure critical angle velocity at different orientations at a given site of bone (Antich, et al., *J. Bone Miner. Res.*, 6:417-426, 1991). Thus, only a single measurement of velocity could be obtained in vivo in cortical bone and trabecular bone. The maximum and minimum velocities could not be reliably determined, and thus an accurate estimation of anisotropy was not possible. Moreover, the original device was cumbersome and time-consuming to use. Lastly, the degree of change in ultrasound velocity with disease shown by the original UCR device was modest as previously mentioned, with the value in postmenopausal osteoporosis being about 13% below that of normal premenopausal state (Antich, et al., *J. Bone Miner. Res.* 8:301-311, 1993).

As used the term "emitting" is used to describe the transmission of an ultrasound wave or pulse by an ultrasound wave transmitter. As used herein the term "receiving" is used to describe the reception by an ultrasound wave receiver of an ultrasound pressure pulse or wave reflected by a material. Together the transmitter and the receiver are described as forming a "transducer" that is able to emit and receive an ultrasound wave reflected from a target material, whether the wave hits the target directly and/or if the wave traverses an ultrasound conductive or transmissive material prior to striking the target, which may be a target point or plane.

As used herein, the term "critical-angle reflection" is used to describe the reflection an ultrasound wave emitted from an ultrasound transmitter after striking a target, where the reflected ultrasound wave travels back toward the ultrasound transmitter and is detected by a receiver array or single receiver. In order to receive or detect an ultrasound wave reflected from a target as a critical-angle reflection, the receivers of the ultrasound wave are at, or about the ultrasound transmitter, e.g., in the direction of the target, whose central area element is generally the common center of the transmitter and the receivers.

The receiver array is connected to one or more signal analyzers that operates to determine at least one characteristic of the received ultrasound wave, e.g., amplitude and phase of the received ultrasound wave. The receivers transmit data to an analyzer, e.g., a computer that includes a code segment that acquires, processes and/or stores data from the two or more receivers with respect to, e.g., the amplitude of the received ultrasound wave; parameters such as maxima, minima (collectively referred to as "extrema"); and edges used to determine various velocities; and/or estimates of the mechanical properties of the target material. With respect to phase, parameters such as the angle of incidence at which phase first appreciably deviates from zero can also be acquired, processed and/or stored and used to calculate and/or estimate the mechanical properties of the target material.

Using data acquired from the receiving array the present invention also includes a system and method for determining, acquiring and automating the detection of the "normal" using, e.g., a computer from data acquired by the receiving array. Automated determination of the normal increases the accuracy of present, past and future measurements to the target, e.g., the surface of the bone from a patient who is taking a drug to treatment osteoporosis or one that can cause bone loss, which permits the use of a rational set of measurements to align the detectors and the bone in a present and future measurements. Consistent, automated determination of the normal is important because the normal defines the zero angle as well as the emitting plane (or plane of scattering), which must contain the normal and the incident wave (I). When the plane and zero are chosen incorrectly, the measurements obtained would be of little value as the angles are not well measured. The method and system of the present invention increase both the accuracy and speed of the determination of the normal, and hence the rapid, precise and repeatable measurement and calculation of critical target data, e.g., a patient's bone quality, with a great reduction in patient's waiting time. By reducing patient's processing time, more patients may be served and cost per determination is reduced.

Furthermore, by acquiring and processing data more accurately, a reduced number of determinations is required to improve patient data, patient compliance and improve patient treatment.

General Description and Mode of Operation of the New UCR Device. The transducer disclosed herein was designed to implement the methodology of ultrasound critical angle reflectometry (Antich, et al., *J. Bone Min. Res.* 6:417-426, 1991; Antich, et al., *J. Bone Min. Res.* 8:301-311, 1993) by making the measurement practical and faster than in previous devices and expands the method to take explicitly into account the anisotropy of bone, assumed to be hexagonally symmetric. The apparatus disclosed herein is designed to make measurements at multiple sites of bone. When made for a specific site, the size of the device should be much smaller, though encompassing the same basic features.

Figure 2:
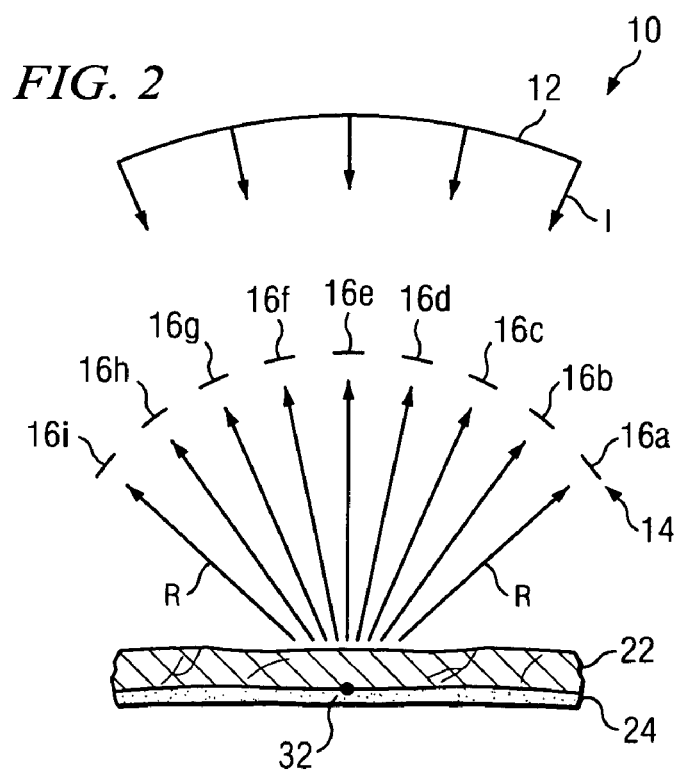

FIGS. 1 and 2 illustrate the general critical-angle of reflection apparatus and method of the present invention. FIG. 1 illustrates an ultrasound transducer 10 functioning as a transmitter 12 and a receiver array 14 that includes two or more receivers (16a, 16b). An ultrasound wave (I) having an angle $\theta_1$ strikes a solid target 22 (e.g., a bone tissue). For convenience, the plane defined by the direction of propagation of the transmitted wave is defined from the Normal (N) to the surface of the target 24, which includes a focal point 32 for the transmitter 12 and the receiving array 14. The reflected (R) ultrasound waves arrive at the receivers 16a, 16b with a pre-defined targeting angle $\theta_2$, which are separated be pre-defined angle $\theta_3$.

FIG. 2 shows another embodiment of the present invention in which the transmitted wave (I) contacts the target 24 after crossing a soft layer 22 (e.g., a soft tissue like skin) and which shows an alternative receiver array 14 that includes an odd number of receivers 16a through 16i after striking the focal point 32 that is about the focal point 32 of the transmitter 12 and the receiving array 14. The receiving array 14 detects simultaneously the reflections R from the target 24 after the pressure waves cross the soft layer 22.

Figure 3:
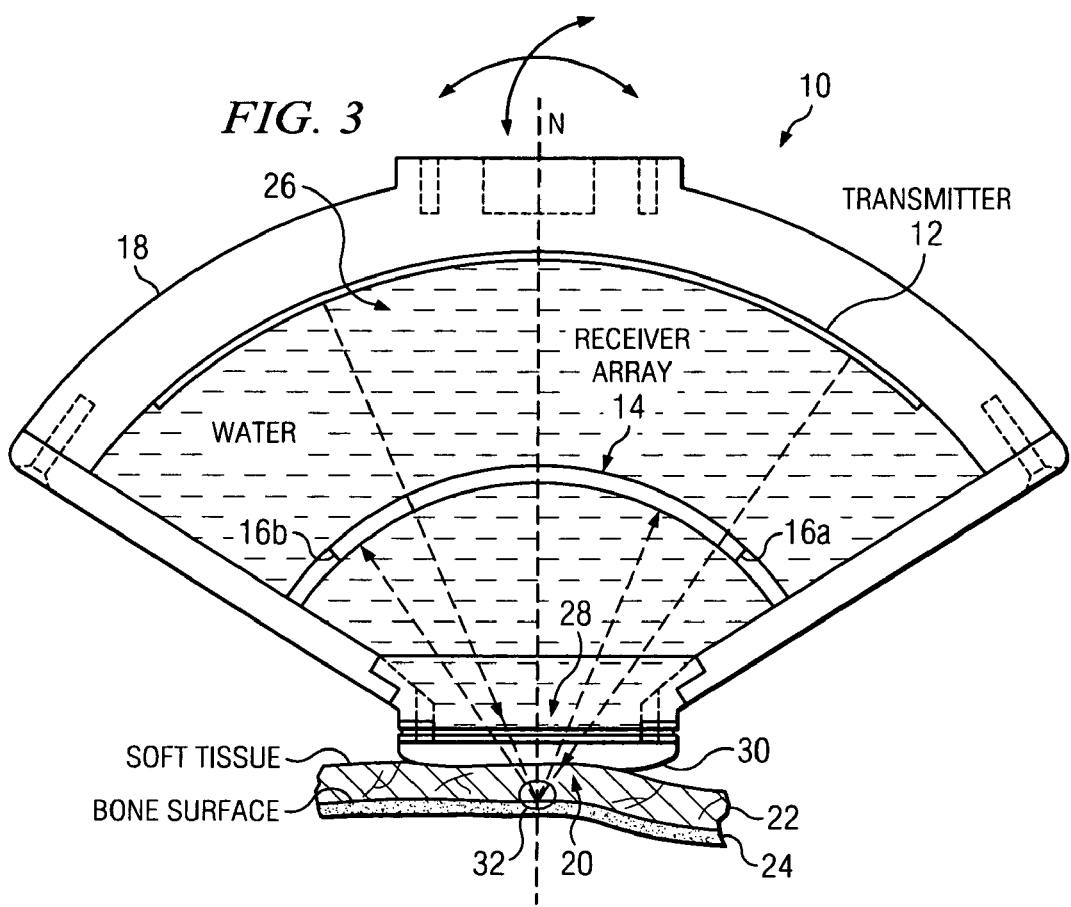
FIG. 3 is a diagrammatic rendering of another embodiment of the present invention that shows a cross-section of the transducer head placed over a bone tissue ready for UCR measurement in close contact with a soft tissue overlying a bone by a latex membrane filled with water.
Figure 4:
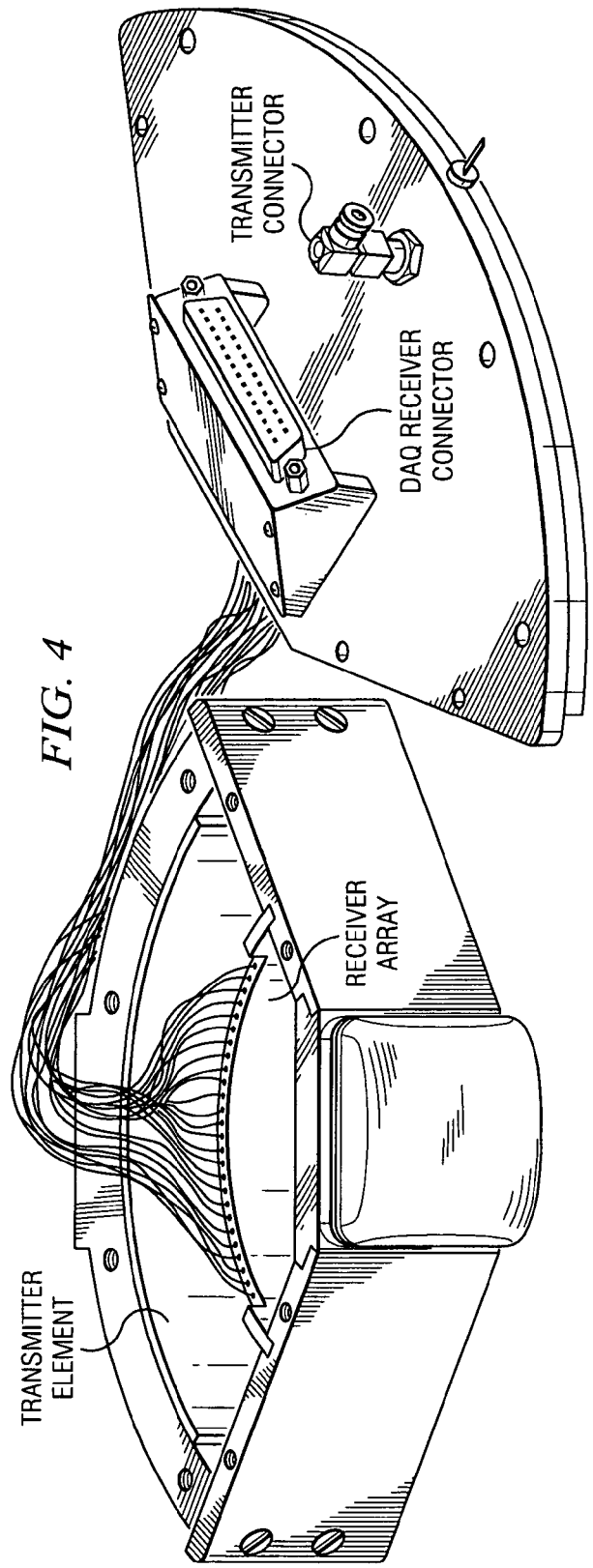
FIG. 4 shows an isometric view of the transducer head, the main body being on the left hand side and the cover on the right. Water fills the volume between transducers and window. A single coaxial cable transports the low current (xA), low voltage (xV) 1.5 MHz signals from the generator to transmitter element and a set of coaxial cables transports the signal from the receiver to the data acquisition system via a multi-element connector.

FIG. 3 is a diagrammatic rendering of another embodiment of the present invention that shows a cross-section of the transducer head 10 ready for UCR measurement in close contact with a target 24. The central elements of the transducer head 10 are a transmitter 12 and a receiver array 14 (together ultrasound elements 12, 14) that includes two or more receivers 16a, 16b in the receiver array 14. The transducer 12 includes two ultrasound elements (12, 14) encased in a housing 18 or container with patient interface 20 depicted here in contact with a soft tissue 22 (e.g., skin) at or about a bone tissue 24 under examination), as shown in FIGS. 2-4. In one example, a single-element transmitter 12 and the 48-element receiver array 14 are separate. Both are sections of a right cylinder with a common axis, subtending 120 degrees. The midpoint of the axial segment is the nominal center of the transducer elements 12, 14. The two ultrasound elements 12, 14 may be mounted with a fixed geometry within, e.g., a water-tight solid housing 18, which is filled with an ultrasound conductive material 26 (e.g., water) and terminates in a window 28 covered by, e.g., a latex membrane 30, in a configuration such that the common center or focal point 32 of the ultrasound elements 12, 14 projects, e.g., about 1.5 cm beyond the window 28. Normal N is shown in FIGS. 1 and 3 as a line that is perpendicular to the bone surface at the focal point.

In operation, the ultrasound conductive material 26 is under a slight pressure controlled by gravity (e.g., by a reservoir of water placed at a slight higher elevation than the transducer head 10 on a support base (not depicted in FIG. 3)) and the latex membrane 30 bulges to, e.g., 0.5 cm beyond the rim of the window 28. When the latex membrane 30 bulge is in contact with the patient's soft tissue 22 (overlying bone 24 being examined), the transducer common center 32 is a virtual point projected under the soft tissue 22 at depth.

Figure 5:
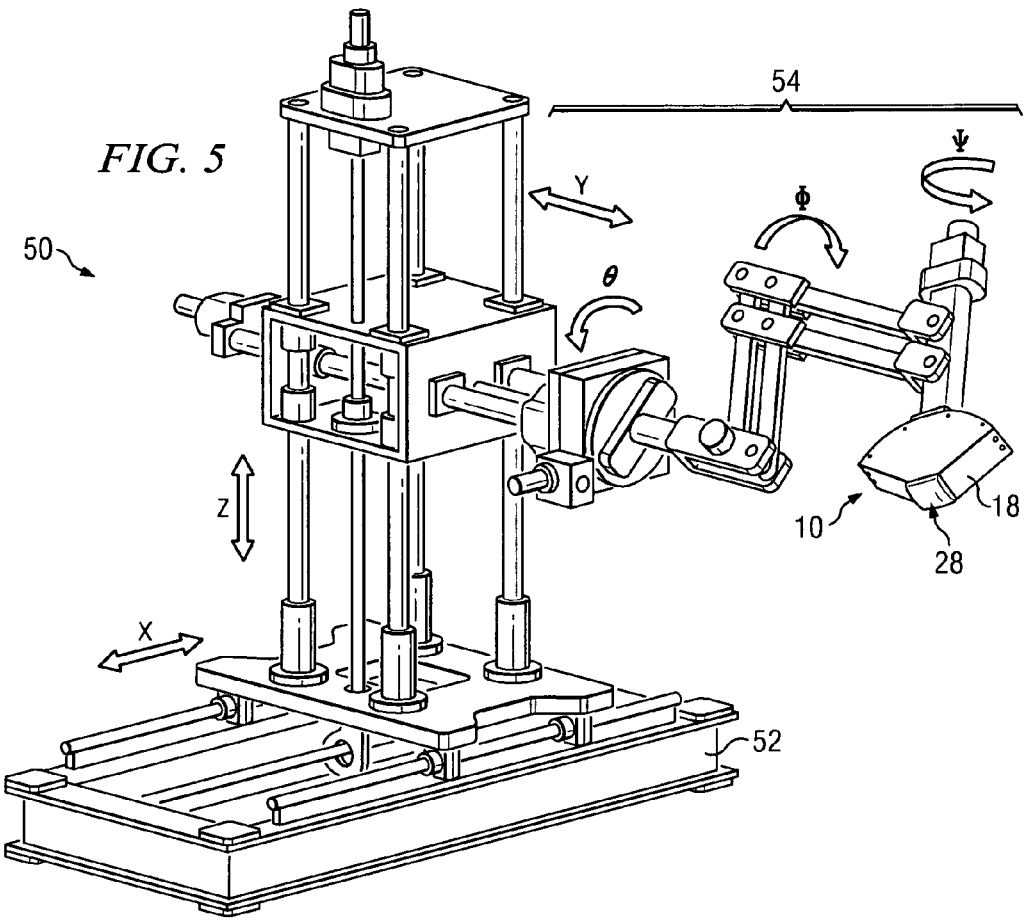
FIG. 5 shows the kinematics of the transducer support arm; three motors mounted on the base and elevator support three-dimensional translations, while three motors mounted on the arm support two tilt rotations ($\theta$ and $\phi$, necessary to identify and select the "normal" to bone) and the rotation of the head around the normal ($\psi$)

A positioning arm 50 for the transducer head 10 is shown in FIG. 5, which is a pantograph that includes two segments shaped as parallelograms, one attached to the base 52 and one supporting the transducer head 10. The arm 54 can be moved vertically and horizontally (three degrees of freedom) by, e.g., motors mounted on the base 52. The arm 54 is articulated so that the transducer head 10 pivots around a fixed point, coincident with the center of the ultrasound elements. In this fashion, the axis of the transducer head 10 can be rotated with two degrees of freedom to assume any orientation around the fixed point.

During an examination, the operator places the transducer head 10 over the site of interest (bone tissue being examined), and the transducer head 10 is advanced by the operator using precise, submillimeter steps of the arm 54 using computer controls until the transducer center is at the surface of the bone under study. This advance, for the heel, is restricted to 0.5-1 cm and the patient's skin remains in contact with the flexible membrane, and does not come in contact with the rim or any other element of the solid surface. Excessive pressure, which occurs, for example, from a sudden movement of the foot that is being measured, causes the advance to stop and the head to retract.

Transducer Head. The ultrasound transducer head includes two elements built on, e.g., PVDF (poly-vinyl-di-fluorene) substrates. The element used as transmitter is single and spans a large interval of degrees from the center, terminating in a latex-covered window. A single coaxial cable transports the low current (xA), low voltage (xV) 1.5-MHz signals from the generator to the transmitter and a set of coaxial cables transports the signal from the receiver to the data acquisition system. A diagram of the head is shown in FIG. 3 and an expanded close-up of the view is shown in FIG. 4, which further includes the leads or connections that transfer a signal acquired by the individual receivers to, e.g., a computer.

While ultrasound has traditionally used ceramics and crystals such as PZT (lead zirconate titanate) and quartz to translate acoustical energy to electrical and visa versa, PVDF is ideally suited in its properties for use in medical ultrasound as it is matched to tissue and pliable. In addition, it is generally cheaper and easier to integrate than traditional ceramics and crystals. The present invention is not limited to the actual materials described herein, as those skilled in the art will know how to match materials to specific target to maximize, e.g., data accuracy, signal strength and/or optimize the signal-to-noise ratio. Compared to PZT, PVDF has two significant advantages as a receiving element. It has a wide frequency response (0.001 to 1 GHz), easily spanning the standard range of biomedical ultrasound. In addition, it has a low acoustic impedance, approaching that of water and human tissue. In contrast, PZT is in general a high Q material that requires multiple matching layers to couple to liquids and soft tissues.

In the UCR transducer head disclosed herein, PVDF may also be used to as the receiving element, because of the ease of working with it and integrating it into receiver arrays. As a film, PVDF can be obtained in a variety of thicknesses, and therefore a variety of sensitivities. With the use of a commercial adhesive (micro-measurements AE-10 thin glue-line epoxy), PVDF films were glued to support structures of non-traditional design and shape in this invention. In addition, unique methods for gluing PVDF films together were developed to create novel detector elements. Also developed were techniques for coupling these multi-layer films to 1D and 2D electric arrays to create novel ultrasound detectors capable of both full waveform reception and excellent beam shape sampling. The receiver array pattern is etched on, e.g., 0.005"-thick fiberglass copper-clad board. The integrated PVDF receiver arrays are integrated with specially designed, multi-channel amplifier and digitization systems that are well-matched to the intrinsic electrical properties of PVDF, which is well matched to human soft tissues.

In order to improve and automate the accuracy of UCR measurements, the system of the present invention was developed. It has been found that patient compliance and reproducible measurement are best achieved when the ultrasound head is oriented perpendicular to the bone surface at each measurement site. The system of the present invention achieves the goals of patient compliance and reproducibility by using two orthogonal rotating (pivoting) motions around the center of the transmitter, one longitudinal and the other transversal. These motions were found to provide minimal requirements for normal alignment. The longitudinal rotation is implemented using a pantograph mechanism that may include two parallelograms, the first one linked to a base shaft and the second to the transducer head. The mechanism is actuated by, e.g., one or more A-max 12V-DC gear motors (Maxon Precision Motors, Inc., Burlingame, Calif.). The actual angular position of the arm is read using a 24,000 steps/revolution optical encoder (model 755A—high precision, Encoder Products Co., Sagle, Id.) for an effective angular resolution of 0.9 minutes of angle (MOA). The range of motion is ±45° from the vertical central position.

The transversal rotation is performed by the base shaft and includes both the transducer head and the pantograph mechanism. The actuating mechanism may include a precision rotary table (model 200RT, Parker Hannifin Corporation, Daedal Division, Irwin, Pa.), and a motor/optical encoder assembly. The angular resolution for the transversal rotation is 0.12 MOA, and the range of motion is ±180°.

In addition to these two pivoting motions, a third rotation around the surface normal is required for the measurement of the anisotropy. The motion may be implemented using the same Maxon 12V DC motor and a 10,000 steps/revolution optical encoder (model 260 accu-coder, Encoder Products Co., Sagle, Id.), for an angular resolution of 2.16 MOA and a range of motion of ±180°.

Precision ball bearings (ABEC 3) may be used for all the rotating parts in order to insure the mechanical precision of the mechanisms. The scanning on the measured surface requires three linear motions oriented along the axis of an orthogonal coordinates system. Each motion is implemented using precision linear ball bearings and shafts, actuated by Maxon 12 V DC motors and precision ball screw and nut mechanisms. The position of each moving element is read by 4,000 steps/rev optical encoders providing a linear resolution of 1.25 µm.

Thus, a total of six degrees of freedom (DOF), three translations and three rotations, are implemented for the precise positioning of the ultrasound transducer head. The motion of each of the six DOF is controlled using a PCI-Flexmotion motion control card (National Instruments, Austin, Tex.). This card uses PID closed loop feedback control algorithm for each axis and allows the implementation of complex 3D trajectories.

The control algorithm monitors the "error" (the difference between the actual position at a certain time and the desired position on the requested trajectory); it will stop the motion of the device if the error becomes larger then a threshold value set at 1 mm for the linear motions and 1° for rotations. Thus, the correct execution of the programmed trajectory of the transducer head is permanently monitored.

In addition, a pressure sensor monitors the contact force between the patient and the elastic membrane of the transducer head. If the contact force becomes larger than 10 N, for example, from a sudden movement of the patient or error in programming of the trajectory of the transducer head, the transducer head is retracted along the direction of the normal to the measured surface, thus preventing potential injury to a subject being examined. Also, the motion control card limits the torque generated by the electrical motors such that the maximum force exerted by the mechanism cannot be larger than 20 N.

UCR Data Acquisition System and Motor Control Electronics. All of the electronic equipment required to operate the UCR system is contained in one 32 inch tall, 19 inch wide, relay rack, with wheels to make it mobile. The tabletop height allows the monitor and computer keyboard to be mounted on top of the rack, and all equipment is connected to a 120-volt, surge protected, rack-mount power strip. There are five rack-mounted modules in the system, containing the following six devices:

(1) Computer. The computer has a 1.3 GHz AMD Athlon motherboard with four PCI slots, and one ISA slot. It has 512 MB of PC100 memory, and a 10GB hard drive. It contains a PCI bus, 48-bit, digital I/O card used to communicate with a delay module (described later) and a proprietary ISA bus interface card, which essentially buffers the address and data lines to transfer data to and from the Data Acquisition Module. A PCI GPIB card is used to program the transmitter, and a PCI card is installed that controls the six DC motors and reads the encoders used to provide the motion in the UCR system. The computer is in a seven-inch high industrial rack-mount case. One or more computers for use with the present invention will generally include code segments that permit data acquisition, normal acquisition and arm positioning, data storage, data processing and a user-interface that permits the user to start a measurement cycle, conduct the data acquisition and capture, interpret the data and graph and/or output the data in a format for immediate analysis, analysis over time, integration with other data and/or data export.

Figure 6:
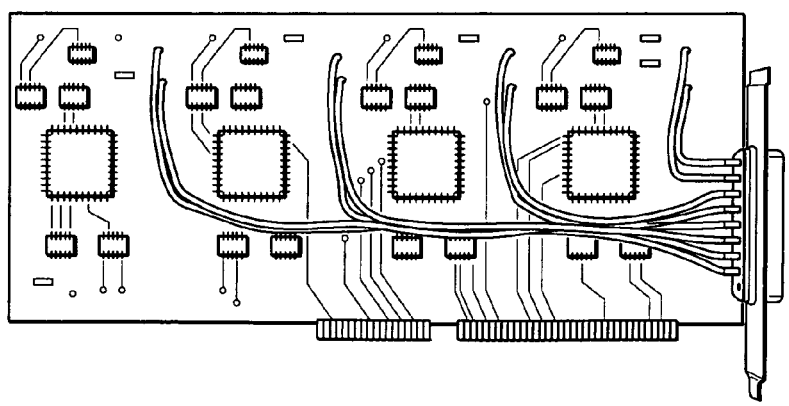
FIG. 6 shows the analog-to-digital acquisition board designed to connect with and receive data from the transducer of the present invention.

(2) Data Acquisition Module. Mounted in a seven inch high case is a (FIG. 6) data acquisition module, which may be a 12-slot ISA passive back plane with connector pin numbers redefined to match signals on a set of proprietary cards developed to digitize the signals from the UCR receiver. Shown in FIG. 6 is an example of Analog-to-Digital card for use with the current invention.

The A/D cards may include four dual eight-bit analog-to-digital converters (Analog Devices AD9059) for a total of eight channels per board. In one example, there are six boards per system, giving forty-eight channels of digitized data, which are sent to the computer for analysis via the ISA bus interface card in the computer. All six A/D cards operate from a 40-MHz, crystal controlled, master clock to assure that all A/D converters start digitizing at the same point on the signal. This gives 25 nanoseconds per point resolution. Sixty-four 8-bit points are collected per acquisition cycle. The digitized data from all A/D converters is read simultaneously into dual-port static ram chips, which is 16 bits wide, organized into two bytes. One-half of the dual A/D converter writes into the upper byte, and the other half writes into the lower byte. This arrangement allows use of the 16-bit ISA to transfer data from two channels at once for faster throughput. The data are stored in the primary port of the ram chip, and read out from the secondary port by the 12-MHz ISA computer bus. Data are simply read as external memory at location C000h, which is a space reserved for add-on cards in the IBM computer architecture. A DIP-switch can change this address if there are conflicts with another board in the computer.

The read-and-write addressing function is performed by an address decoder card on the passive back plane. The address decoder card generates the master clock and the write address for the ram chips, and also decodes the memory address for each board. The decoder card in the Acquisition chassis is connected to the ISA bus interface card in the computer chassis by a 50-pin ribbon cable. Linear type power supplies are used to supply the 1 ampere, minus 5 volts and the 10 ampere, plus 5 volts required by all six A/D cards, in order to eliminate the noise generated by the more commonly used switching regulator power supplies.

(3) Transmitter. The transmitter, which is used to excite the transmit section of the UCR transducer, includes two components: a rack-mounted, synthesized function generator (Stanford Research Systems model DS345), and a Mini-Circuits model ZHL-32A RF power amplifier which is mounted in the back of the rack with its 24-volt power supply. The transmitter configuration puts out a 24-volt peak-to-peak, 3-cycle, 1 MHz, sine wave burst into a 50-ohm load. The transmitter has the capability of being programmed by the computer via a GBIB interface mounted in one of the PCI slots.

(4) Preamplifier Assembly. The function of the preamplifiers is to amplify the low-level (millivolt range) signals from the receiver section of the UCR transducer to match the 100-millivolt peak-to-peak input sensitivity of the A/D cards. The A/D converters have, e.g., a 1-volt sensitivity, with a X10 amplifier at each A/D input. The preamplifiers have a gain of 100 (40 dB), which gives an overall gain of 1000. There may be eight channels per board, with six boards in the system, for a total of 48 channels. Each channel contains a 50-ohm pulse transformer to match the input impedance of the A/D cards and prevent ground loops by isolating the preamplifier assembly. The input impedance of the preamplifiers (Analog Devices AD844) is set at 10,000 ohms to match the high impedance of the PVDF film used in the receiver construction. As depicted, the preamplifier cards are mounted in an EIA-standard sub-rack with a built-in linear, plus and minus 15-volt power supply. The input connectors are standard DB37S, as are the connectors on the A/D card inputs.

(5) Motor Controller Chassis. There are six, 12-volt DC motors, each with their own position encoder, used to control the motion of the platform, arm, and transducer assembly in the UCR system. The motor controller chassis contains power supplies, drivers for the motors, and an interface to the motor controller board, in the computer. The motor drives are National Semiconductor LM1875 power amplifiers used in a direct-coupled configuration. This arrangement allows clockwise and counter-clockwise rotation at any velocity, and the 4-phase position encoders provide precise positioning.

(6) Programmable Delay Generator. It is programmed by three of the 8-bit ports on the PIO card in the computer, and simply sets a delay between the software instruction to fire the transmitter and the signal to start the data acquisition. The velocity of sound through the water enclosed in the transducer head is about 1.5 Km per second, with a temperature dependence that can be directly calibrated. Data acquisition is delayed to allow for appropriate propagation of the ultrasonic wave. The above arrangement prevents the digitization of all the dead time between the transmitted and received signals. The counter is programmable up to 4096 microseconds, with 100-nanosecond resolution. It may include three 74F163 pre-settable binary counters, and a 10-MHz crystal clock. It is housed in a small chassis, with power supply, in the back of the rack.

Operational Description of Data Acquisition. The Scalable Multichannel Data Acquisition System (SMDAS) is a high frequency digital system for collecting data in the standard ultrasonic frequency range (50 kHz to 10 MHz). The SMDAS hardware component generally includes multiple channels with two stages: pre-amplification and digitization. The system is scalable with a granularity of, e.g., 8 channels.

The SMDAS is a triggerless, computer-controlled system, based on a low-cost, 8-bit, 60-MHz analog-to-digital converter. Because traditional UCR used three-cycle, 4-MHz pulses, a 40-MHz solution was chosen so as to permit 10 times oversampling of these signals. A sampling memory of 64 samples (1.6 µs) provides sufficient storage for each channel. A total of 48 channels were chosen because each channel maps to a specific angle of incidence, and all pressure critical angles and 2-gamma shear dynamics occur for angles less than 40 degrees in solids of interest.

Digitization Subsystem. The heart of digitization is the AD9059 (Analog Devices, Norwood, Mass.), a dual channel IC package capable of sampling at 40 million samples per second. Although an external reference voltage can be applied to this chip, the AD9059 can also self-generate the required level to operate the internal pipeline of comparators. With self-referencing enabled, the AD9059 accepts two single-ended inputs with a voltage range between 1.5 and 2.5 Volts. Upon cycling with a TTL compatible clock, the 16 digital output pins on the AD9059 will output 8-bit digital samples for the two input channels. While digital crosstalk is negligible, the AD9059 is rated with 1.5 bits of noise. For 8 channels, a two-layer printed circuit board was designed, wire-wrap tested, and built (Alpha Printed Circuits, Mesquite, Tex.) to accommodate four independent subsystems of two channels. For each AD9059, a 16-bit dual port static RAM (CY7C133, Cypress Semiconductor, San Jose, Calif.) with ~25 ns access time is used to record the 64 samples for two channels, although in principle only 128 bytes of memory should suffice. The PCBs are equipped with DB37F connectors (Amphenol, Wallingford, Conn.), and each channel is routed to a pre-amplification stage with a coaxial wire to avoid the noise associated with a trace on the PCB.

Before digitization, each channel passes through an operational amplifier (CLC440, ComLinear/Nationional Semiconductor, Santa Clara, Calif.) with a gain of 10. The amplification stage expects all inputs to be 50 ohms in impedance. Each board has a 98-pin on-board edge connector designed to fit into a 14-slot ISA standard backplane (JDR Microdevices, San Jose, Calif., part number BP141) mounted in a separate computer chassis. For each board, there is also a selectable board identification jumper needed for reading from a given card. A special decoder board also in the bus associates each digitizing board with a memory address relative to some selectable base address, in steps of 128 bytes (0x080h). The decoder board is in turn connected with a parallel ribbon cable to a buffer board on the computer system's ISA bus. If the base address is set to be in the x86 architecture's high memory area (that is, 0xD0000h to 0xE0000h), this configuration allows direct memory access to samples stored in the memories for each individual channel. If a 2-byte read is utilized, data can be read for two channels simultaneously. In the initial design, sampling was initiated by a memory write to the base address. It should be noted that memory reads are limited in time by clocking of the ISA bus, which on recent motherboards was maximized at 12.5 MHz.

Pre-Amplification Subsystem. Although the digitization subsystem includes some amplification, it is often necessary to condition signals from transducers with additional amplification. With certain transducers, there may also be issues involved with impedance matching, especially for high impedance, polymer based piezoelectric system. A high impedance input amplification system was designed and built around a 44-pin EIA card subrack (Vector Electronics, North Hollywood, Calif.). Each amplifier cards uses high impedance operation amplifiers (Analog Devices, AD844) to amplify signals ideally from PVDF transducers. With a nominal gain of 100 for 10,000 ohm input impedance, these amplifiers also resist oscillations that can occur with impedance mismatches. The AD844 has a bandwidth-gain product of over 300 MHz, so signal distortion should be negligible at typical ultrasonic frequencies. Output of each channel is transformer (Mini Circuits, Brooklyn, N.Y., part number T1-1) coupled to prevent catastrophic ground loops. The EIA rack is connected to the chassis containing the digitization subsystem with shielded, coaxial cables.

Signal Generation and Timing. In order to have precise timing between pulse generation and the start of the sampling, it was necessary with the original SMDAS design to have a computer system with little or no overhead. With a data acquisition window of 1.6 µs, precise timing could be guaranteed with a real time operating system (RTOS). With a Windows (Microsoft, Redmond, Mass.) or Linux brand operating system, the system timing granularity is on the order of 1 millisecond. Rather than going with an expensive embedded solution, the flexibility of an industry standard operating system was retained, and the timing for signal generation and sampling was moved to a custom-made external module. The timing module is enclosed in a rack mountable case. It contains three 4-bit binary counters operating at 10 MHz, programmable with the digital output from a PIO card (PCI-DIO48H, Measurement Computing, Middleboro, Mass.). Twelve bits of programmability at 10 MHz translate to a delay range of 409.6 µs. For typical ultrasonic velocities in water and soft tissues, this window accounts for propagations up to 60 cm. After the pulse generator firing is commenced, the counters complete their programmed delay, and then a TTL level signal is transmitted via external co-axial cable to the decoder board in the DAQ chassis to commence sampling.

Software for Data Acquisition. The SMDAS software component includes, e.g., several layers of libraries for accessing the SMDAS hardware component. The SMDAS software offers entry points at several layers of system programming, providing maximum flexibility for application development and future systems integration.

Memory Mapping. As designed, the data acquisition board memory that contains sampled data is mapped to a physical memory address in the upper memory area of the Intel x86 architecture. By reading at this address and storing the information in a variable array, the sampled data can be transferred from board memory to system memory without need for complex communications or system drivers. Because reading of sampled data is ultimately multiplexed across the ISA bus, it is most efficient to read in two-byte words to maximize the bus bandwidth. After transfer, the 8-bit samples must be separated. On a modern microprocessor, such as a Pentium (Intel Corporation, Santa Clara, Calif.) or Athlon (AMD, Sunnyvale, Calif.) class chips, this separation should be accomplished in a single clock cycle instruction. An arbitrary bit shift (also known as a barrel shift) or a bit-wise AND operation can be used to extract the upper or lower 8 bits from the 16-bit word.

To facilitate the memory mapped read, a dynamic linked library (DLL) was created using Visual Studio Professional 6.0 (Microsoft Corporation, Redmond, Wash.) using the C programming language. This low level library provides a function for reading a 2-byte word at an arbitrary address in the upper memory area (unsigned short int 1v48chdaq(int addr)) and two functions for extracting upper and lower samples (unsigned char left/right(unsigned short int a)). This portable DLL can, e.g., be linked into Windows applications developed in a variety of programming languages, and by cycling through memory address all sampled data can be transferred to system memory for analysis or for saving to storage media.

Noise Reduction. The visual programming environment LabVIEW (National Instruments, Austin, Tex.) was chosen for development of data acquisition software due to its rapid development scheme, its ease of use, and its recognition as an industry standard. In order to maximize flexibility for future applications, an intermediate library of "virtual instruments" (VIs) was developed using a bottom-up approach where a special global VI contains parameters common to all components (that is, number of channels, base memory address).

At the lowest level, the "download 2 channels" VI is attached to the DLL described above and cycles through the appropriate memory addresses to transfer 128 bytes to system memory. Each channel possesses repeatable error that is measurable with the pre-amplification stage disabled or the open inputs. Fourier analysis of averages of this residual indicates contributions at 40 MHz and its subharmonics. This is entirely consistent with reference voltage noise due to a lack of shielding on the address lines for the buffer memories. Because 6 address lines are required, one would not be surprised to find noise at the fundamental and at the 5 subharmonics (20, 10, 5, 2.5, and 1.25 MHz).

The "download 2 cleaner channels" VI subtracts this repeatable signal from sampled data, and the resultant noise is consistent with the manufacturer's specifications. An application can either generate these average background waveforms itself, or it can use the default ones produced by the "calibrate average background waveforms" VI. The "download n cleaner channels" VI packages multiple channels into an n by 64 matrix.

The pipeline architecture of the AD9059 requires a 1-MHz minimum sampling rate. At slower rates, the internal registers are degraded, and the sampling is extremely inaccurate. Because the transfer of one block of 64 two-channel words occurs at ISA bus speeds (in the order of 10 MHz), the effective rate for sequential acquisitions is less than 200 kHz. Thus, the first 5 samples of every acquisition of each channel may be suspect. Because the granularity of the time delay subsystem is 0.1 µs, it is convenient to drop the first 8 samples (0.2 µs).

Multiple Frame Acquisition. The real power of this intermediate library is its ability to construct time windows larger than the 1.6 µs given by 64 samples. In one determination using steady-state dynamics, it is possible to adjust the delay time between sequential acquisitions so that they are properly aligned in time. The "acquire" VI uses the "set delay time" VI to form contiguous frames from "download n cleaner channels". The process is repeated a number of times, with each sequential acquisition appending to the previous set of data. The resulting output of N channels and M 1.4 µs frames gives a matrix of dimensions Nx(56xM). It should be noted that the rate-limiting step in the data acquisition process is the transfer of information across the ISA bus. An increase in the number of frames and time window raises the scan time, which in general grows at a linear rate.

Stochastic Frame Acquisition. In some imaging situations, the alignment of contiguous time frames will lead to spurious signals. This problem is especially evident with large blocks of time (order of 100 µs) in scenarios where secondary reflections or reverberations from early pulses are captured in later frames. These signals cannot be removed by taking an average. In order to minimize these unwanted data, it is sometimes necessary to gather multiple frames in a stochastic manner. For a given time window, the 1.4 μs frames are selected at random from a list until exhausted and the window is filled. If this method is repeated and averaged, the cross-correlated signals from separate frame pulses may be eliminated.

Figure 7:
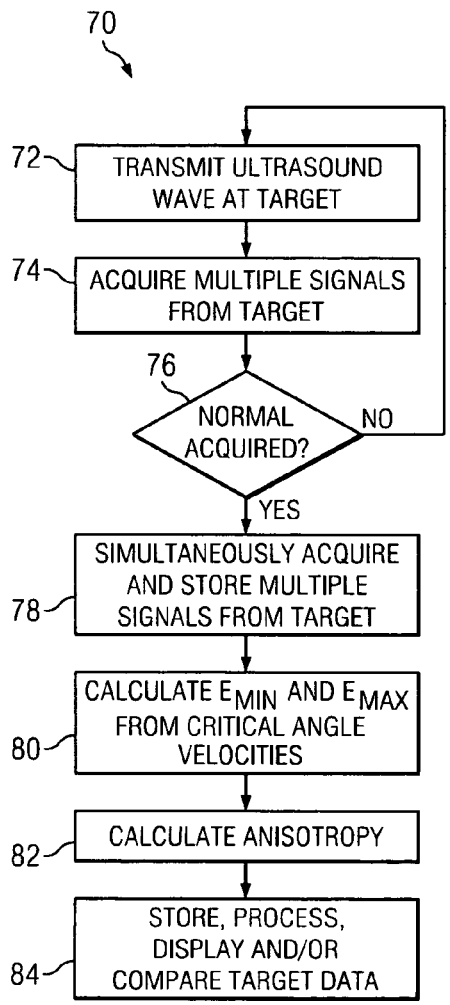
FIG. 7 is a basic flowchart that summarizes the basic data acquisition model of the present invention.

In operation, the system of the present invention is summarized in the flowchart 70 of FIG. 7. In step 72, an ultrasound wave or pulse is transmitted toward a target, e.g., a bone, and the reflected signals are captured by two or more receivers in step 74. Based on the signals acquired from the receptors a determination is made as to whether the normal was found is made at step 76, which is made by a computer that directs, e.g., the articulated arm to either move the transducer or begin data acquisition. If the normal was found, then the final data from the target is acquired simultaneously in final data acquisition step 78, and the results stored as an analog signal or a digital equivalent. Based on the data acquired from the final acquisition step 78, the Emax and Emin are calculated at step 80 to determine the ultracritical reflectometry data of the target, from which the anisotropy may be calculated in step 82. Finally, the raw data, processed data and/or the calculated results may be stored, processed, displayed, printed and /or compared to earlier or later target data and calculations to provide the user with useful results at step 84.

Figure 8:
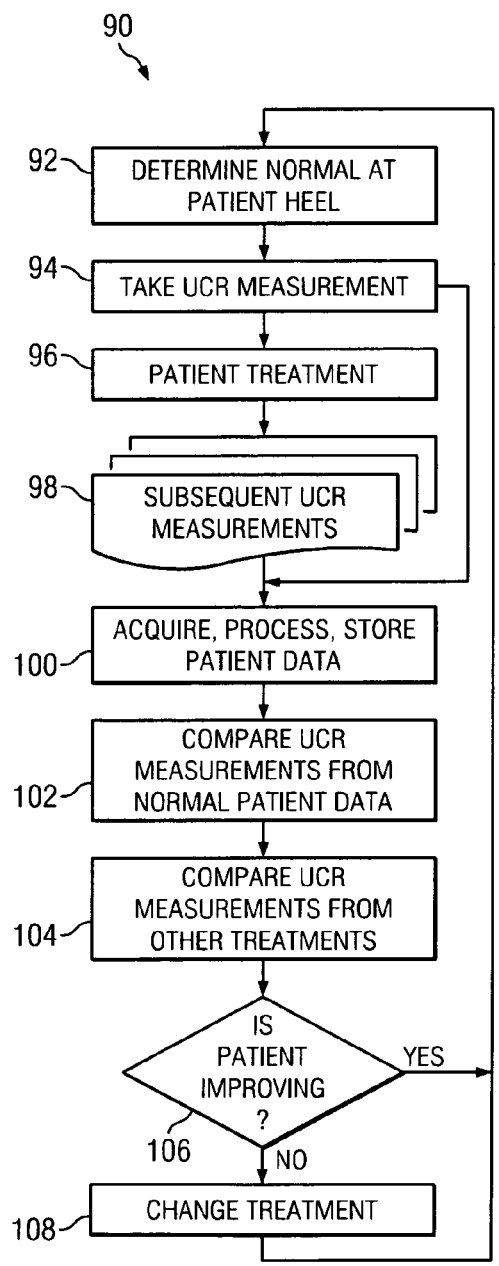
FIG. 8 is a basic flowchart that shows the use of the present invention in patient evaluation and treatment.

In FIG. 8, the ultracritical reflectometry data acquisition transducer, method and system are used in flowchart 90 to make a determination for treatment of a patient. In step 92, the normal is determined for bone, in this example at the heel. Upon acquisition of the normal, the transducer takes the critical UCR measurements. If the patient is concurrently or about to begin a treatment regimen, that occurs at step 96, with subsequent measurements taken at time-intervals (e.g., weekly, bi-weekly, monthly, depending on the physicians instructions and type of treatment) in step 98. Data from before patient treatment (step 94) and subsequent treatments (step 98) are acquired, processed and/or stored as patient data (step 100). The measurements, data and processed patient information is then compared at step 102 with normal patient data, and with the UCR measurements from the same or other treatments (step 104) from the same and/or other patients and a determination is made to see if the patient is improving at step 106. If the patient is improving then they may be returned to the bone scanning regime. If the patient is not improving or getting worse, then the physician can direct a change in treatment and the patient is returned to the monitoring regime (step 108).

A similar flow chart may be used to follow effects of certain treatments that are suspected of causing bone loss or of impairing bone quality, e.g., steroids, high dose fluoride and anticonvulsants.

The collection of reflected signal begins when bone surface is reached. This time is operationally defined by an abrupt increase in the reflected signal over all angles. The operator then initiates a series of automated steps to accurately identify the normal. These steps control the acquisition of reflected angular spectra from at least two orthogonal directions on the bone surface. For each direction the plane of the normal is found by tilting the transducer head until the integrated signal is maximum; the intersection of the two orthogonal planes defines the normal. The reflected spectra (signals at all receiver elements) are then obtained by rotating the head around the normal in 15-degree intervals over 120 degrees; the two orientations at which the first critical angle is smallest and greatest identify the two principal axes of bone.

Calculation of Key Indices of Bone Quality from UCR. In general practice, measurements are made at three discrete areas of bone tissue being examined. At each site, multiple critical angle velocities (v) are obtained over 120 degrees. The data for v are mathematically fitted to the formula: $v^2=a+bx^2+cx^4$, where x=cos (orientation), and $v^2$ is elasticity normalized to a density of 1 g/cc. From the resulting graph, the minimum ($E_{min}$) and maximum ($E_{max}$) elasticities of trabecular and cortical bone are calculated as a measure of bone material quality. (Henceforth, the term "elasticity" will be used interchangeably with the term "elasticity coefficient".) From the area-under the curve of v data, "integrated" or "mean" elasticity ($E_{int}$) is calculated. $E_{int}$ is essentially the same as the square of average velocity. Anisotropy (A) is calculated as the ratio of corresponding maximum and minimum elasticities.

Clinical Application of New UCR Device. (1) Development of Adynamic Bone Disease During Bisphosphonate Treatment of Osteoporosis. Bisphosphonates (such as Fosamax® and Actonel®) are widely used for the treatment of postmenopausal osteoporosis throughout the world. This treatment is known to increase bone density and decrease fractures (Liberman, et al., *N. Engl. J. Med.*, 333:1437-1443, 1995). The primary action of this drug is to inhibit bone resorption (destruction). There is secondary reduction in bone formation that lags behind the fall in bone resorption during the first 1-3 years of treatment. During this period, a gain in bone mass occurs resulting in increased bone density. The inhibition of fractures has been ascribed to this rise in bone density. From studies in experimental animals, however, a concern has been raised that bisphosphonate may produce a profound suppression of bone turnover that could cause microdamage and compromise bone quality (Li, et al., *Calc. Tissue Intern.*, 69:281-286). Moreover, in human beings, it has been suggested that chronic bisphosphonate treatment may impair bone quality from marked suppression of bone turnover, causing increased rate of fracture after long-term bisphosphonate treatment (Ott, *J. Clin. Endo. Metab.* 86:1835, 2001).

The study summarized below was undertaken in order to determine if such complication can occur in human beings, using the apparatus, method and system disclosed herein. Using the present invention, it was discovered that long-term bisphosphonate treatment causes "adynamic bone disease," a histologic appearance of bone displaying a marked suppression of bone turnover with virtual absence of cellular activity (Odvina, et al., *J. Bone Miner. Res.*, publication expected September 2003).

A transiliac crest bone biopsy was performed in 6 postmenopausal osteoporotic women (49-76 years), who developed fractures after they had been on long-term bisphosphonate treatment for 3-7 years. Besides bisphosphonate, 3 patients took hormone replacement therapy, 2 prednisone (one for fibromyalgia, the other for asthma), 4 vitamin D, and all 6 patients received calcium supplements. Fractures occurred in finger in 1 patient, pelvis in 3, hip in 1, foot in 1, and femur in 2. In four patients, bone biopsy was obtained because patients displayed delayed healing of fractures (of ischium, femur, pelvis) for 3 months to 2 years while maintained on bisphosphonate treatment. In two patients, the biopsy was taken shortly after they developed fractures (sacrum, pubic rami, rib), because the physician felt that the index of suspicion for adynamic bone disease was high.

Figure 9A:
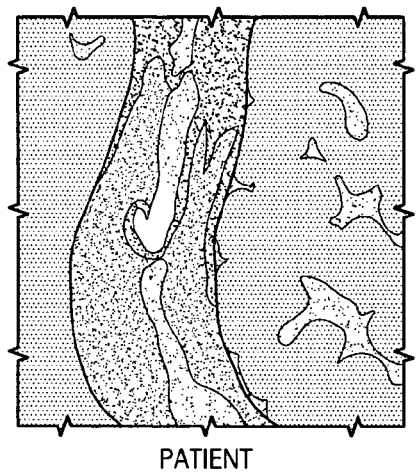
FIGS. 9A and 9B are microphotographs of ultraviolet light illumination that shows the absence of tetracycline labeling in a patient on long-term bisphosphonate treatment (9A), and normal labeling in a normal subject (9B)
Figure 9B:
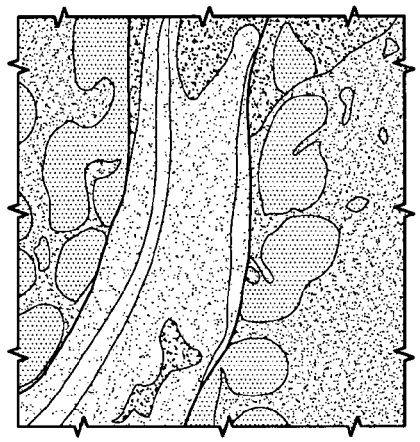

Histamorphometric findings in trabecular bone are summarized in Table 1. As shown in FIGS. 9A and 9B, bone formation were markedly diminished with low osteoblast surface (Ob.S/BS) and absence of double tetracycline label (dLS) and absent or diminished single label (sLS) in all specimens. Before a biopsy was obtained, tetracycline was given in two courses 10 days apart. Tetracycline is picked up in areas of active bone formation, imparting yellow fluorescent lines under ultraviolet light illumination. FIGS. 9A and 9B are microphotographs of a single trabeculus under ultraviolet light illumination that shows the absence of tetracycline labeling in a patient on long-term bisphosphonate treatment (9A), and normal labeling in a normal subject (9B). Two courses of tetracycline were given 10 days apart. Tetracycline is picked up in area of active bone formation, imparting yellow lines under polarized light microscopy. The distance between two labels represent the amount of new bone mineralized over 10 days. Absence of tetracycline labeling indicated markedly impaired bone formation. Bone resorption (destruction) parameters (ES/BS and Oc.S/BS) were also decreased in 3 patients. A similar trend was observed in cortical bone (data not shown).

mean (integrated) cortical and trabecular elasticities were within the range of values in normal premenopausal women, indicative of eventual correction of defective bone quality after stopping bisphosphonate treatment.

In two patients, UCR analysis of the heel was performed in vivo when they presented with fractures while still on bisphosphonate treatment. Mean cortical elasticity was decreased by 25% and 26%, and mean trabecular velocity by 16% and 15%, compared to mean values for normal premenopausal women. The remaining two patients underwent bone biopsies elsewhere and were not available for UCR measurements.

The finding of reduced elasticities of cortical and trabecular bone in patients with adynamic bone disease from bisphosphonate treatment strongly suggests that abnormal structural derangement in bone (shown on histomorphometry) is correlated with impaired bone quality, affirming the previously stated hypothesis.

(3) Detection of Impaired Bone Quality by New UCR in vivo Among Patients on Long-Term Bisphosphonate Treatment. Using the new UCR device disclosed herein, the ultrasound elasticity of cortical and trabecular bone was measured at multiple orientations in the calcaneous in vivo. UCR analy-

TABLE 1

Histomorphometric Findings in 6 Patients with Adynamic Bone Disease After Long-Term Bisphosphonate Treatment

| Parameters | Patient 1 | Patient 2 | Patient 3 | Patient 4 | Patient 5 | Patient 6 | Normal Mean ± SD |
|---|---|---|---|---|---|---|---|
| BV/TV (%) | 9.4 | 8.9 | 14.3 | 15.2 | 12.2 | 10.9 | 21.17 ± 4.9 |
| OV/BV (%) | 0 | 0.05 | 0.42 | 0.66 | 0 | 0.89 | 0.38 ± 0.25 |
| Oc.S/BS | 0 | 0.12 | 1.0 | 0.3 | 0.17 | 0.29 | 0.7 ± 0.7 |
| ES/BS (%) | 0.85 | 1.7 | 9.5 | 9.3 | 2.1 | 1.3 | 4.0 ± 2.0 |
| Ob.S | 0 | 0.19 | 1.7 | 0 | 0 | 3.6* | 4.4 ± 3.2 |
| dLS/BS (%) | 0 | 0 | 0 | 0 | 0 | 0 | 4.3 ± 2.9 |
| SLS/BS (%) | 0 | 0.3 | 0.58 | 0 | 0 | 0 | 6.0 ± 4.1 |

Abbreviations:
BV = bone volume;
TV = total volume;
OV = osteoid volume;
Oc.S/BS = osteoclastic surface/bone surface;
ES = eroded surface;
Ob.S = osteoblactic surface;
dLs = double-label tetracycline label;
sLS = single tetracycline label.
*= probably falsely high, since osteoblasts appeared flat and inactive.

The results suggest that bisphosphonate may cause adynamic bone disease with markedly reduced bone formation. "Bone turnover", a process by which "old" or damaged parts of bone are removed and replaced by new healthy bone, is markedly suppressed as well. Following a chronic suppression of bone turnover, bone microdamage may accumulate (Li, et al., Calc. Tissue Intern. 69:281-286, 2001). This explanation can account for recurrent fractures that display delayed healing.

(2) UCR Reflectometry in vivo Among Patients with Adynamic Bone Disease. Bone elasticity was measured in vivo in the calcaneus by new UCR in two patients from the preceding study with adynamic bone disease on bisphosphonate treatment, 8 months and 12 months after withdrawal of bisphosphonate treatment. At the beginning of this study the UCR device was not available. In the former patient, the mean (integrated) cortical and trabecular elasticities were depressed by 15.4% and 27.1%, respectively, from the mean of normal premenopausal women. In the latter patient, the sis using the present invention was performed in 14 normal postmenopausal women, 9 with postmenopausal osteoporosis on conventional treatment (untreated PO), and 25 on bisphosphonate treatment (mean duration 3.5 years). Values were expressed as percentage of values in 14 normal premenopausal women (Table 2). Mild or no decreases (<5%) were observed in normal postmenopausal women. A mild-moderate reduction in elasticity (~10%) was disclosed in untreated postmenopausal women. In bisphosphonate treatment, trabecular elasticity (both maximum and minimum) significantly declined by about 15%, and cortical elasticity decreased by about 25%. Anisotropy of cortical and trabecular bone decreased during bisphosphonate treatment, owing to a more prominent decline in maximum elasticity. Thus, bone material became less anisotropic after this treatment, signaling an abnormal character of bone. Integrated cortical elasticity decreased significantly by 25.9% in cortical bone and by 17.5% in trabecular bone from normal premenopausal values following bisphosphonate treatment.

TABLE 2

Trabecular and Cortical Elasticities Measured in vivo by UCR

| Elasticity | | Normal Postmenopausal | Osteoporotic Untreated PO | BISPHOS |
|---|---|---|---|---|
| Trabecular | $E_{min}$ | 100.1 ± 3.1 | 94.2 ± 5.7 | 85.1 ± 5.5[+] |
| | $E_{max}$ | 98.6 ± 4.3 | 89.9 ± 6.2* | 82.3 ± 6.0[+] |
| | $E_{int}$ | 98.3 ± 3.6 | 91.8 ± 5.9* | 82.5 ± 5.6[+] |
| | A | 98.5 ± 3.4 | 95.3 ± 1.4** | 96.8 ± 3.4[+] |
| Cortical | $E_{min}$ | 97.4 ± 5.0 | 91.7 ± 1.8[+] | 75.4 ± 5.5[+] |
| | $E_{max}$ | 96.8 ± 5.9 | 87.4 ± 1.4[+] | 72.1 ± 6.9[+] |
| | $E_{int}$ | 97.4 ± 4.7 | 90.8 ± 2.0[+] | 74.1 ± 6.2[+] |
| | A | 99.4 ± 4.3 | 95.4 ± 2.7* | 95.6 ± 6.8** |

Elasticities are presented as percentage of normal premenopausal women.
*$p < 0.05$;
**$p < 0.01$;
[+]$p < 0.001$ vs. normal premenopausal women.
PO = postmenopausal osteoporosis;
BISPHOS = bisphosphonate;
$E_{max}$ = maximum elasticity;
$E_{min}$ = minimum elasticity;
$E_{int}$ = integrated elasticity;
A = anisotropy;
± = plus/minus standard deviation.

Much of the decline in elasticity occurred during the first 3 years of bisphosphonate treatment. During bisphosphonate treatment, bone elasticity was independent of heel bone mineral density obtained simultaneously by dual photon x-ray absorptiometry as shown in FIG. 10.

Figure 10:
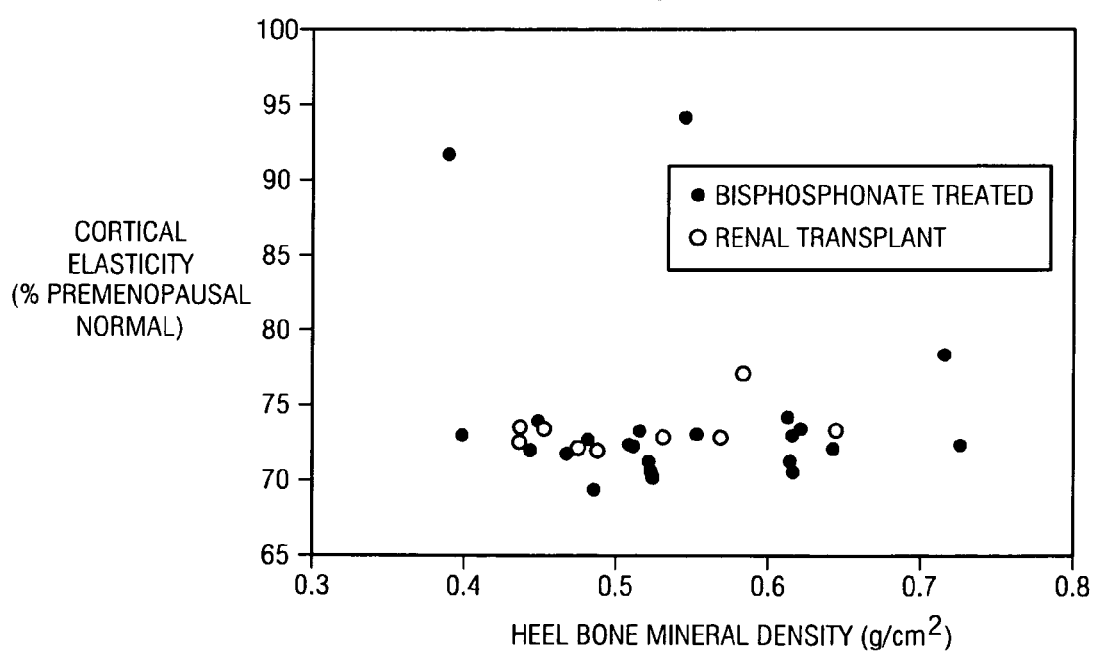
FIG. 10 is a graph that shows independence of bone elasticity from bone density during bisphosphonate treatment and in renal transplantation.

FIG. 10 also shows that bone elasticity is independent of bone elasticity in patients with renal transplant taking steroid, as in those treated with bisphosphonate. The integrated (mean) elasticity coefficient of cortical bone by new UCR and bone density by dual photon x-ray absorptiometry were simultaneously measured in the calcaneus in vivo. There were two "outliers" with elasticity coefficients that were much higher than in the rest. One of them was a patient in whom bisphosphonate treatment had been stopped for 1 year. Otherwise, the elasticity of cortical bone did not vary very much over a wide range of bone density.

This finding confirms earlier conclusion (Antich, et al., J. Bone Miner. Res., 8:301-311, 1993) that UCR measures material or intrinsic bone quality, not bone density at the organ level. In normal pre- and postmenopaual women and in postmenopausal osteoporotic patients on conventional treatment, elasticity was modestly correlated with bone density.

(4) Inferior Bone Quality in Renal Transplantation Shown by New UCR. Ultrasonic analysis was performed in vivo using the new UCR device in 9 patients who underwent kidney transplantation and taking steroids (Table 3). In renal transplantation, a condition known to be associated with weakened bone and propensity to fractures, maximum and minimum elasticities in trabecular bone were significantly lower by 15-17% compared to normal premenopausal women. Cortical elasticities were reduced by 25-29%. The decline in maximum elasticities was more prominent than that of minimum elasticities, resulting in significantly lower anisotropy, compared with the normal premenopausal state. Findings were remarkably similar to those of bisphosphonate treatment (Table 2 vs. Table 3).

TABLE 3

Trabecular and Cortical Elasticities in Renal Transplantation and During Treatment with Sustained-Release Sodium Fluoride

| Elasticity | | RT-St | SR-NaF |
|---|---|---|---|
| Trabecular | $E_{min}$ | 85.1 ± 1.8[+] | 96.3 ± 4.6 |
| | $E_{max}$ | 83.2 ± 1.8[+] | 93.3 ± 2.5[+] |
| | $E_{int}$ | 83.4 ± 1.4[+] | 94.9 ± 2.1[+] |
| | A | 97.8 ± 2.0* | 97.1 ± 3.7 |
| Cortical | $E_{min}$ | 75.0 ± 2.4[+] | 95.0 ± 6.2 |
| | $E_{max}$ | 71.4 ± 2.6[+] | 95.4 ± 6.9 |
| | $E_{int}$ | 73.2 ± 1.5[+] | 94.1 ± 4.8** |
| | A | 95.2 ± 2.1[+] | 100.5 ± 5.1 |

Elasticities are presented as percent of normal premenopausal women.
*$p < 0.05$;
**$p < 0.01$;
[+]$p < 0.001$ vs. normal premenopausal women.
RT-St = renal transplantation on steroids;
SR-NaF = sustained-release sodium fluoride;
$E_{max}$ = maximum elasticity;
$E_{min}$ = minimum elasticity;
$E_{int}$ = integrated elasticity;
A = anisotropy;
± = plus/minus standard deviation.

(5) Improved Bone Quality Following Treatment with Sustained-Release Sodium Fluoride. The treatment of osteoporotic patients with sustained-release sodium fluoride was shown to increase trabecular bone velocity when measured by the original UCR device (Zerwekh, et al., J. Bone Miner. Res. 6:239-244, 1991; Antich, et al., J. Bone Miner. Res. 8:301-311, 1993, see also U.S. Pat. No. 5,228,445, relevant portions incorporated herein by reference). Ultrasonic analysis of the heel was performed in vivo using new UCR device in 8 patients with osteoporosis after treatment with sustained-release sodium fluoride. The elasticity coefficients of cortical and trabecular bone from patients undertaking this treatment resided between the values in normal postmenopausal women and postmenopausal osteoporotic patients on conventional treatment (Table 2 vs. Table 3). Anisotropy in patients undergoing sustained-release sodium fluoride treatment was found to be intact. Thus, the new UCR device can detect improved bone quality and unaltered anisotropy by sustained-release sodium fluoride.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

References

U.S. Patent Documents

| 5,038,787 | Aug. 13, 1991 | Antich et al. |
| 5,197,475 | Mar. 30, 1993 | Antich et al. |
| 5,228,445 | Jul. 20, 1993 | Pak and Antich |

Other Publications

Antich et al., "Measurement of mechanical properties of bone material in vitro by ultrasound reflection: methodology and comparison with ultrasound transmission", *Journal of Bone and Mineral Research*, 6:417-426 (1991).

Antich et al., "Measurement of intrinsic bone strength in vivo by reflection ultrasound: correction of impaired quality with slow-release sodium fluoride and calcium citrate", *Journal of Bone and Mineral Research*, 8:301-311 (1993).

Li et al., "Bisphosphonate treatment suppresses not only stochastic remodeling but also the targeted repair of microdamage", *Calcified Tissue International*, 69:281-286 (2001).

Liberman et al., "Effect of oral alendronate on bone mineral density and the incidence of fractures in postmenopausal osteoporosis", *New England Journal of Medicine*, 333:1437-1447 (1995).

NIH Consensus Conference, "Osteoporosis, diagnosis and therapy", *Journal of American Medical Association*, 285: 785-795 (2001).

Odvina et al., "Adynamic bone disease during bisphosphonate therapy: should we be concerned?" *Journal of Bone and Mineral Research* (September, 2003).

Ott, "Fractures after long-term alendronate therapy, *Journal of Endocrinology and Metabolism*, 86:1835 (2001).

Pak et al., "Treatment of postmenopausal osteoporosis with slow-release sodium fluoride: final update of a randomized trial", *Archives of Internal Medicine*, 123:401-408 (1995).

Richer et al., "Impaired bone quality in bisphosphonate (BISPHOS) treatment and in renal transplantation", *Journal of Bone and Mineral Research* (September, 2003).

Zerwekh et al., "Assessment by reflection ultrasound method of the effect of intermittent slow-release sodium fluoride-calcium citrate therapy on material strength of bone", *Journal of Bone and Mineral Research*, 6:239-244 (1991).

What is claimed is:

1. An ultrasound apparatus comprising:
   an ultrasound transmitter;
   two or more receivers that form a receiver array wherein the receiver array and the transmitter are concentric about a line that passes through a focal point of the receiver array and the transmitter and wherein the line is perpendicular to a plane in which the receiver array and the transmitter are disposed, and wherein the receiver array is adapted to detect simultaneously the reflected ultrasound energy from both cortical and trabecular portions of a bone target; and
   a processor connected to the transmitter and receivers of the ultrasound apparatus, wherein the processor calculates one or more reflected spectra from each receiver and calculates from the spectra critical angles for the cortical and the trabecular portions of the bone target.

2. The ultrasound apparatus of claim 1, wherein the transmitter is concave in at least two dimensions.

3. The ultrasound apparatus of claim 1, wherein the two or more receivers form part of a concave array in at least two dimensions.

4. The ultrasound apparatus of claim 1, wherein the transmitter and the two or more receivers are concave and concentric.

5. The ultrasound apparatus of claim 1, wherein the transmitter is concave and the two or more receivers are concave and the transmitter and the two or more receivers are concentric about a common focal point.

6. The ultrasound apparatus of claim 1, wherein the receivers are further defined as a receiving array and the array comprises 2, 4, 8, 16, 24, 36, 48, 64 or 128 independent receivers.

7. The ultrasound apparatus of claim 1, wherein the array system is comprised of a single transmitter and a 48-element receiver array located in a housing connected to a processor, wherein the receiver array detects simultaneously an ultrasound wave across 120 degrees from a point of examination that is at or about the focal point of the transmitter and the processor calculates and displays the ultracritical angle of the ultrasound wave.

8. The ultrasound apparatus of claim 1, further comprising a housing for the transmitter and the at least two receivers, the housing having at least one opening at or about the focal point of the transmitter and receivers.

9. The ultrasound apparatus of claim 1, further comprising:
   a housing for the transmitter and the at least two receivers, the housing having at least one opening;
   a latex membrane at or about the opening of the housing; and
   an ultrasound conductive material within the housing.

10. The ultrasound apparatus of claim 9, wherein the ultrasound conductive material comprises water.

11. The ultrasound apparatus of claim 9, further comprising a pressure detector in communication with the ultrasound conductive material, which detects the increase in pressure within the housing that may break the latex membrane.

12. The ultrasound apparatus of claim 1, further comprising a computer-controlled positioning arm connected to the ultrasound apparatus, wherein movement of the ultrasound apparatus permits accurate positioning of the ultrasound apparatus on a point of examination.

13. The ultrasound apparatus of claim 1, further comprising at least one computer comprising the processor connected to the transmitter and receivers of the ultrasound apparatus, the computer comprising at least one code segment that displays the spectra for the critical angles for the cortical and the trabecular bone.

14. The ultrasound apparatus of claim 13, wherein the computer further comprises at least one code segment that determines critical-angle velocities, and fits them to a linear-quadratic equation for the determination of at least two principal coefficients of elasticity.

15. An ultrasound critical angle reflectometer comprising:
   an ultrasound transmitter; and
   two or more receivers that form a receiver array wherein the receiver array and the transmitter are concentric about a line that passes through a focal point of the receiver array and the transmitter and wherein the line is perpendicular to a plane in which the receiver array and the transmitter are disposed, wherein the focal point is targeted to be a bone, and wherein the receiver array is adapted to detect simultaneously the reflected ultrasound energy from a portion of the bone target at multiple angles including a normal; and
   a processor connected to the transmitter and receivers of the ultrasound critical angle reflectometer, wherein the processor processes one or more reflected spectra from each receiver to calculate critical angles for cortical and trabecular regions of the bone target.

16. The ultrasound apparatus of claim 15, wherein the transmitter is concave in at least two dimensions.

17. The ultrasound apparatus of claim 15, wherein the receiver array comprises a concave array in at least two dimensions.

18. The ultrasound apparatus of claim 15, wherein the receiver array comprises 2, 4, 6, 12, 24, 36 or 48 independent receivers.

19. The ultrasound apparatus of claim 18, wherein the ultrasound apparatus comprises a single transmitter and the receiver array connected to the processor, wherein the receiver array detects simultaneously an ultrasound wave across 120 degrees from a point of examination that is at or about the focal point of the transmitter and the processor calculates a velocity of the ultrasound wave and displays the velocity data.

20. The ultrasound apparatus of claim 15, further comprising a housing for the transmitter and the receiver array, the housing having at least one opening at, about or adjacent to, the focal point of the transmitter and receiver array.

21. The ultrasound apparatus of claim 15, further comprising:
   a housing for the transmitter and the receivers, the housing having at least one opening;
   a latex membrane at or about the opening of the housing; and
   an ultrasound conductive material within the housing.

22. The ultrasound apparatus of claim 21, wherein the ultrasound conductive material comprises water.

23. The ultrasound apparatus of claim 15, further comprising a computer-controlled positioning arm connected to the ultrasound apparatus, wherein movement of the ultrasound apparatus permits accurate positioning of the ultrasound apparatus on a point of examination.

24. The ultrasound apparatus of claim 15, further comprising a pressure detector positioned to contact the ultrasound conductive material which detects when excessive pressure is applied to a latex membrane enclosing ultrasound conductive material within the housing.

25. The ultrasound apparatus of claim 15, further comprising at least one computer connected to the transmitter and the receiver array.

26. The ultrasound apparatus of claim 25, wherein the computer comprises at least one code segment that gathers one or more reflected spectra from the receiver array and calculates from the spectra one or more critical angles for a cortical and a trabecular bone.

27. The ultrasound apparatus of claim 25, wherein the computer comprises at least one code segment that determines critical angle velocities, and fits the critical angle velocity to a linear-quadratic equation for the determination of at least two principal coefficients of elasticity.

28. A method for non-invasively, in vivo and simultaneously determining a maximum and minimum elasticity coefficients and an anisotropy of a cortical and a trabecular bone target comprising the steps of:
   measuring a critical angle from the cortical and the trabecular bone target using an ultrasound apparatus comprising:
   an ultrasound transmitter;
   two or more receivers that form a receiver array wherein the receiver array and the transmitter are concentric about a line that passes through a focal point of the receiver array and the transmitter and wherein the line is perpendicular to a plane in which the receiver array and the transmitter are disposed, and wherein the receiver array is adapted to detect simultaneously the reflected ultrasound energy from cortical and trabecular portions of a bone target; and
   a processor connected to the transmitter and receivers of the ultrasound apparatus, wherein the processor calculates one or more reflected spectra from each receiver and calculates from the spectra critical angles for the cortical and the trabecular portions of the bone target; and
   deriving the maximum and the minimum elasticity coefficients and the anisotropy of the cortical and the trabecular bone targets.

29. A method for non-invasively, in vivo, and simultaneously determining a maximum and minimum elasticity coefficients and an anisotropy of a cortical and a trabecular bone target comprising the steps of:
   measuring a critical angle from the cortical and the trabecular bone target using an ultrasound critical angle reflectometer comprising:
   an ultrasound transmitter; and
   two or more receivers that form a receiver array wherein the receiver array and the transmitter are concentric about a line that passes through a focal point of the receiver array and the transmitter and wherein the line is perpendicular to a plane in which the receiver array and the transmitter are disposed, wherein the focal point is targeted to be a bone, and wherein the receiver array is adapted to detect simultaneously the reflected ultrasound energy from a portion of the bone target at multiple angles including a normal; and
   a processor connected to the transmitter and receivers of the ultrasound critical angle reflectometer, wherein the processor processes one or more reflected spectra from each receiver to calculate critical angles for cortical and trabecular regions of the bone target; and
   deriving the maximum and the minimum elasticity coefficients and the anisotropy of the cortical and the trabecular bone targets.

* * * * *

UNITED STATES PATENT AND TRADEMARK OFFICE
CERTIFICATE OF CORRECTION

PATENT NO. : 7,611,465 B2  Page 1 of 1
APPLICATION NO. : 10/630330
DATED : November 3, 2009
INVENTOR(S) : Peter P. Antich et al.

It is certified that error appears in the above-identified patent and that said Letters Patent is hereby corrected as shown below:

Col. 1, line 52
Replace "tions presented situations" with --tions present situations--

Col. 2, line 14
Replace "more practical and faster" with --more practically and faster--

Col. 2, line 67
Replace "of device on a point" with --of the device on a point--

Col. 14, line 20
Replace "rack-mount power strip" with --rack-mounted power strip--

Signed and Sealed this

Ninth Day of March, 2010

David J. Kappos
*Director of the United States Patent and Trademark Office*